United States Patent [19]

Nyberg et al.

[11] Patent Number: 4,888,098
[45] Date of Patent: Dec. 19, 1989

[54] METHOD AND ARTICLES EMPLOYING ION EXCHANGE MATERIAL

[75] Inventors: Eric D. Nyberg, Belmont; Ken A. Klingman, Menlo Park; Jeff Curtis, San Francisco; Ray F. Stewart, Redwood City, all of Calif.

[73] Assignee: Raychem Corporation, Menlo Park, Calif.

[21] Appl. No.: 17,375

[22] Filed: Feb. 20, 1987

Related U.S. Application Data

[63] Continuation-in-part of Ser. No. 932,763, Nov. 19, 1986, abandoned, which is a continuation-in-part of Ser. No. 831,758, Feb. 20, 1986, abandoned.

[51] Int. Cl.[4] .......................................... G01N 27/26
[52] U.S. Cl. .................. 204/1 R; 204/182.3; 204/1 T; 204/412; 204/415; 204/418; 204/282
[58] Field of Search ................. 204/415–418, 204/433, 296, 1 R, 1 T, 252, 254, 182.4, 182.3, 183.3, 301, 302, 282; 429/129, 62, 90–93; 324/426, 431–432, 438–439, 441, 450, 62–65 R

[56] References Cited

U.S. PATENT DOCUMENTS

| 2,741,591 | 4/1956 | Dewey, II et al. | 204/1 R |
|---|---|---|---|
| 3,297,484 | 1/1967 | Niedrach | 136/86 |
| 3,645,884 | 2/1973 | Gilliland | 204/301 |
| 3,846,270 | 5/1970 | Muto et al. | 204/405 |
| 4,032,452 | 6/1977 | Davis | 210/243 |
| 4,100,331 | 7/1978 | Ingham et al. | 429/13 |
| 4,210,501 | 7/1980 | Dempsey et al. | 204/129 |
| 4,263,115 | 4/1981 | Kessler et al. | 204/416 |
| 4,468,306 | 8/1984 | Freeman et al. | 204/182.4 |
| 4,537,668 | 8/1985 | Gaussens et al. | 204/296 |

FOREIGN PATENT DOCUMENTS

| 0028142 | 5/1981 | European Pat. Off. . | |
| 0056283 | 7/1982 | European Pat. Off. | 204/418 |
| 0113387 | 7/1984 | European Pat. Off. . | |
| 2625443 | 12/1976 | Fed. Rep. of Germany . | |
| 133370 | 8/1982 | Japan | 429/90 |
| 112266 | 6/1985 | Japan | 324/432 |

OTHER PUBLICATIONS

Electro–Regenerated Ion-Exchange Deionization of Drinking Water, NTIS PB–270–910 (1977).
Chemical Microstructures on Electrodes, L. R. Faulkner, Chemical Engineering News, Feb. 27, 1984, pp. 28–45.

*Primary Examiner*—John F. Niebling
*Assistant Examiner*—Ben C. Hsing
*Attorney, Agent, or Firm*—Yuan Chao; Edith A. Rice; Herbert G. Burkard

[57] ABSTRACT

An electrode, preferably of a conductive polymer, has on its surface, preferably over all of its surface, an ion exchange material, preferably of significant thickness. Such a coated electrode may be used for sensing the presence or measuring the concentration of an ionic species, or for removal from or release of an ionic species into an electrode.

8 Claims, 8 Drawing Sheets

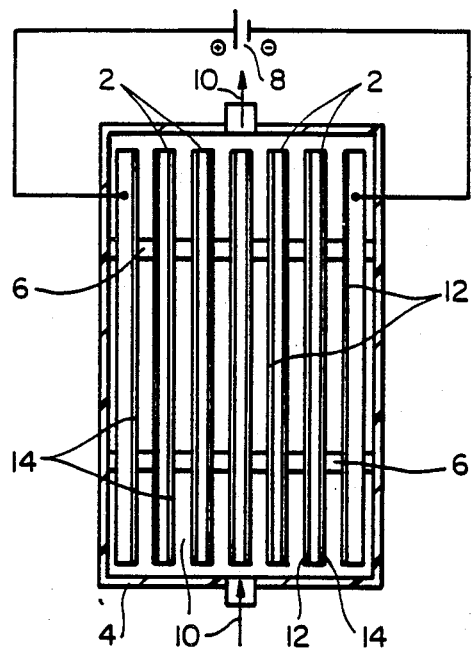
FIG_1
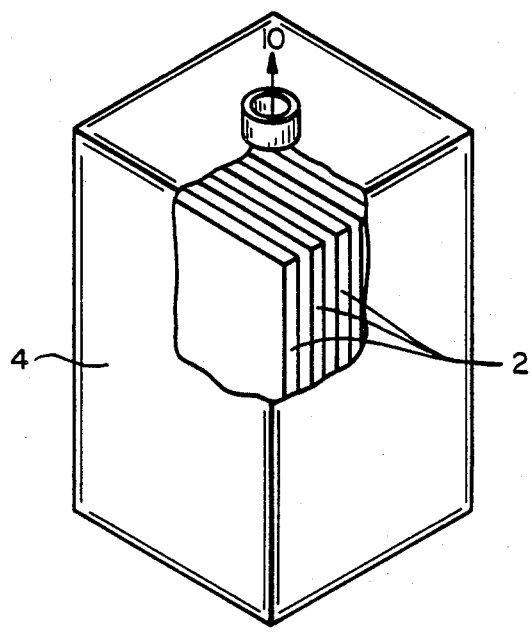
FIG_2

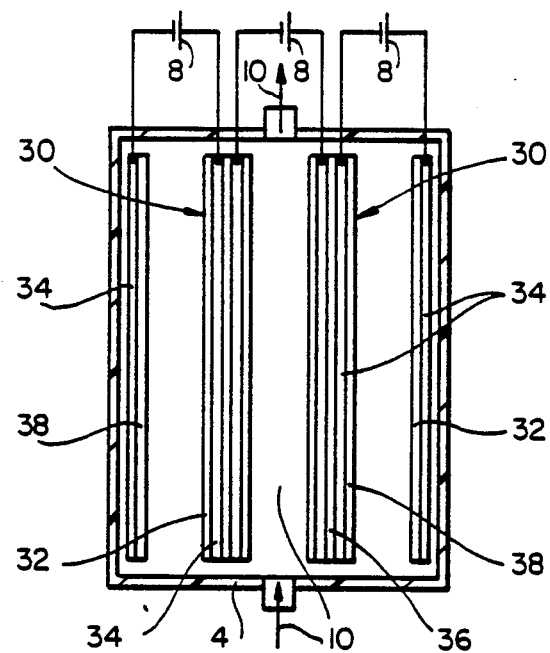
FIG_3
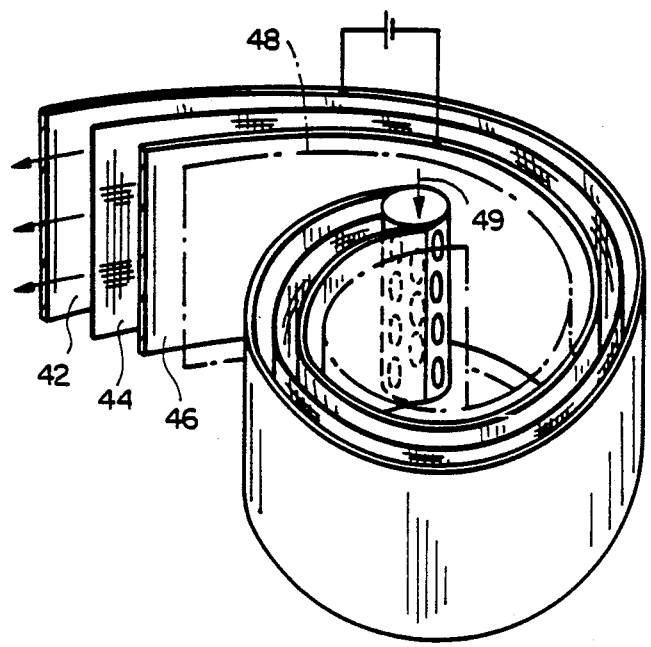
FIG_4

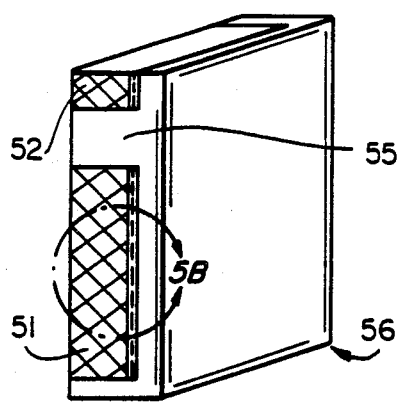
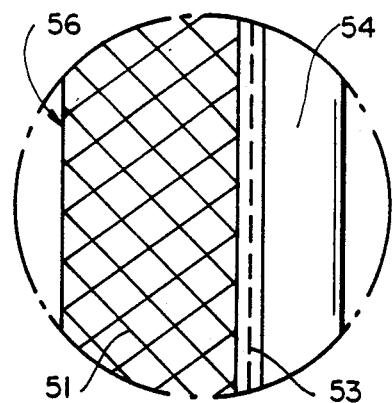
FIG_5A  FIG_5B
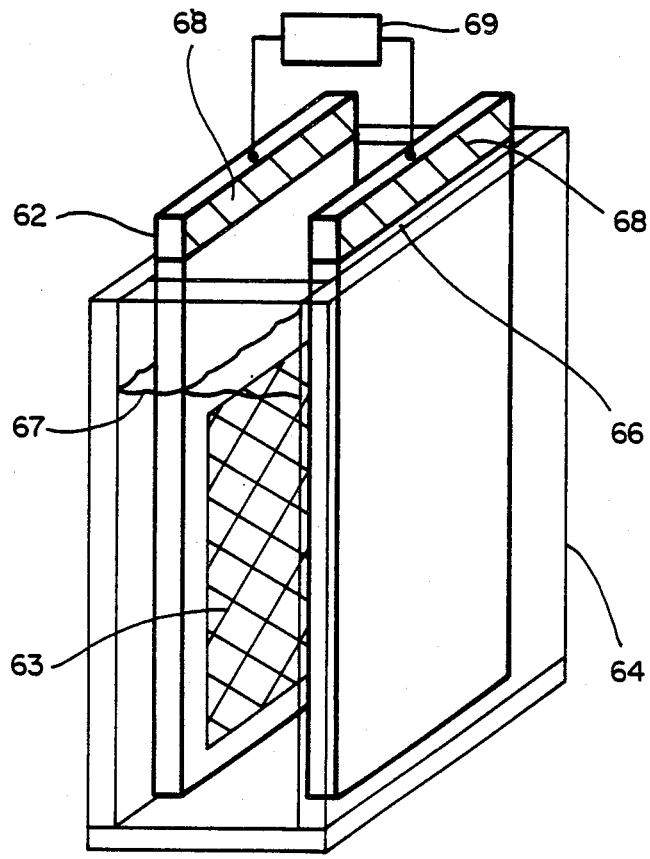
FIG_6

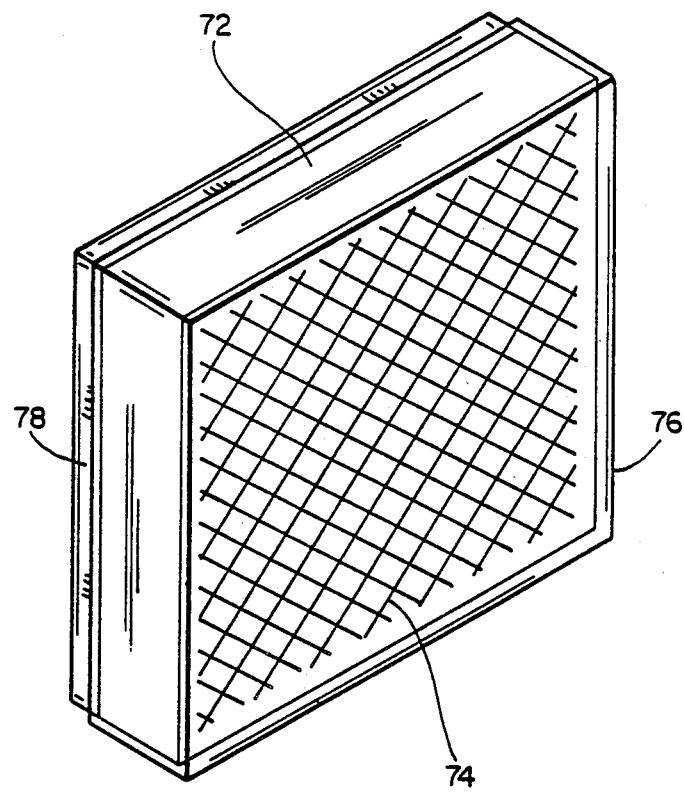
FIG_7
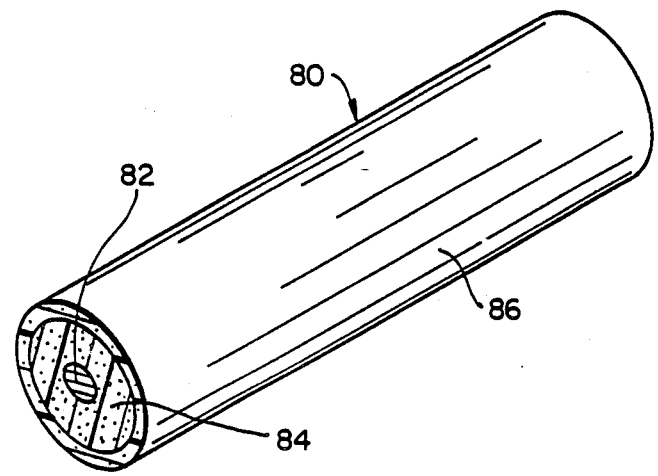
FIG_8

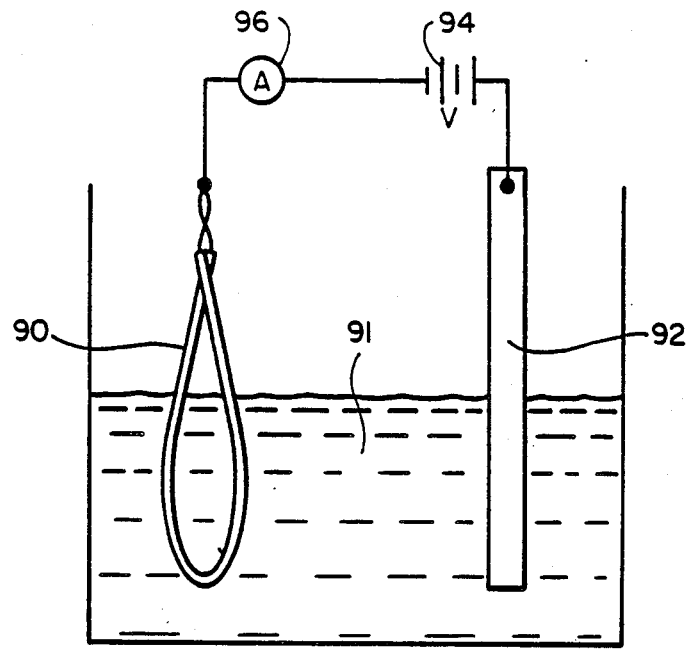
FIG_9
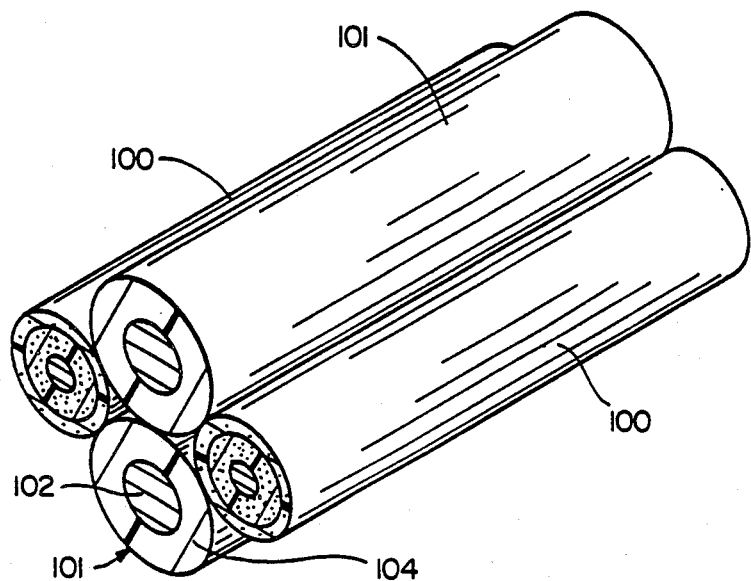
FIG_10

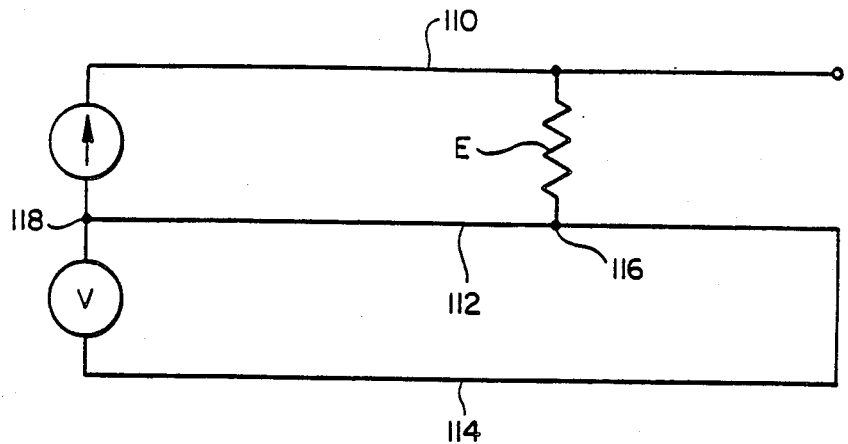
FIG_11
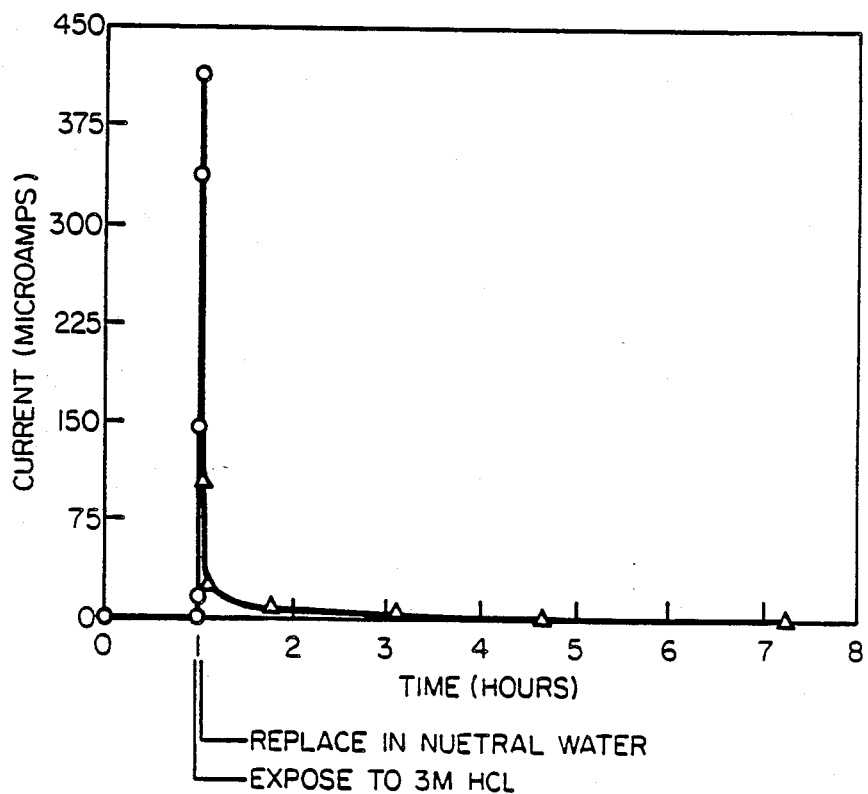
FIG_12

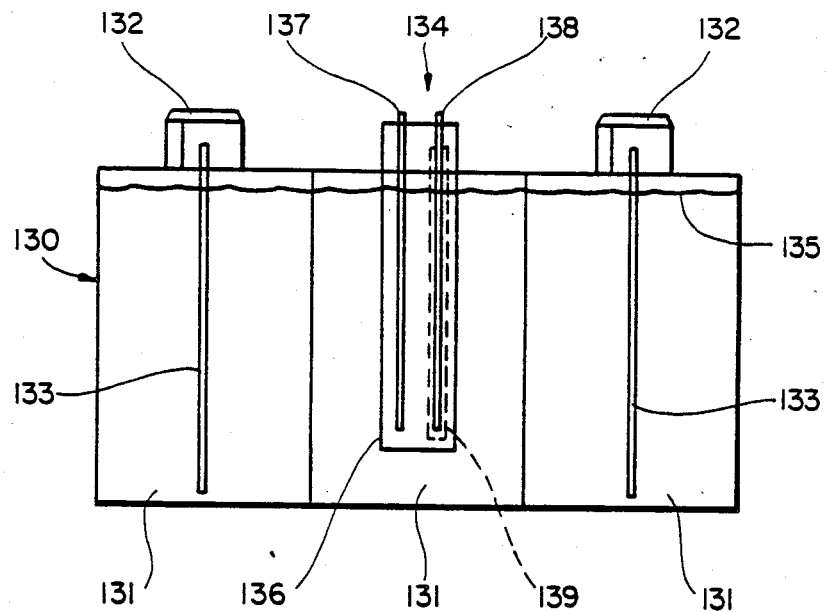
FIG_13
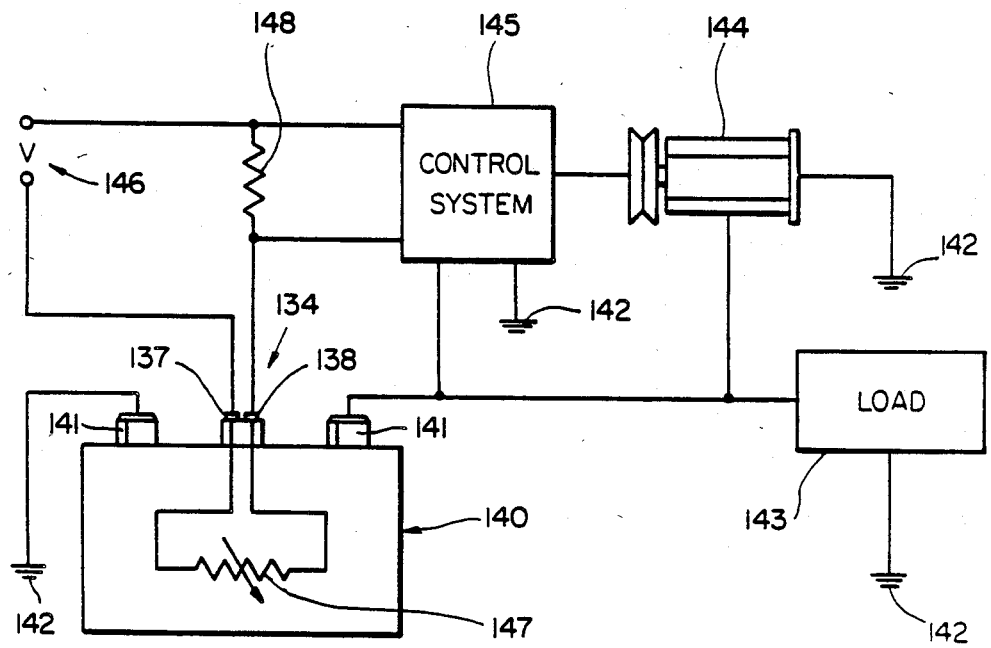
FIG_14

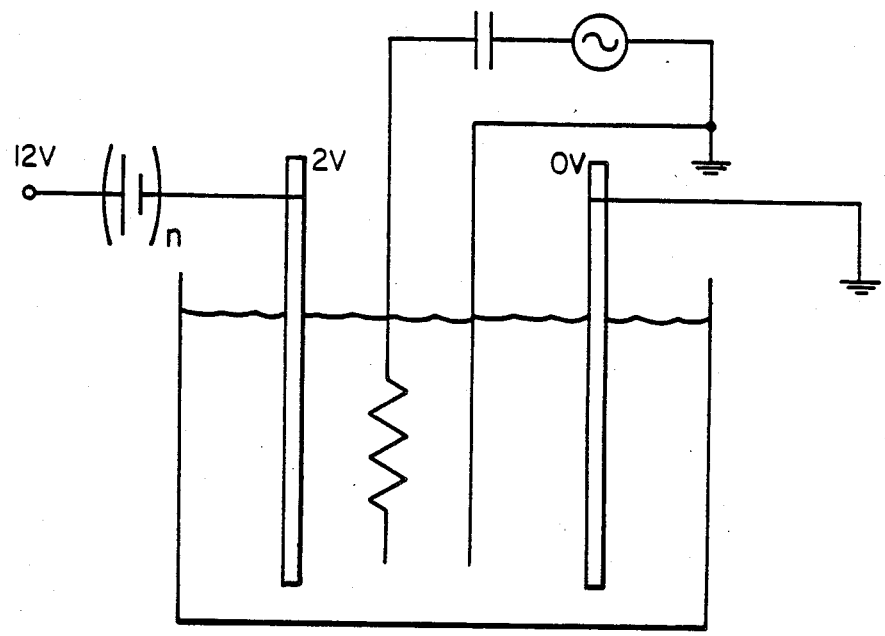
FIG_15A
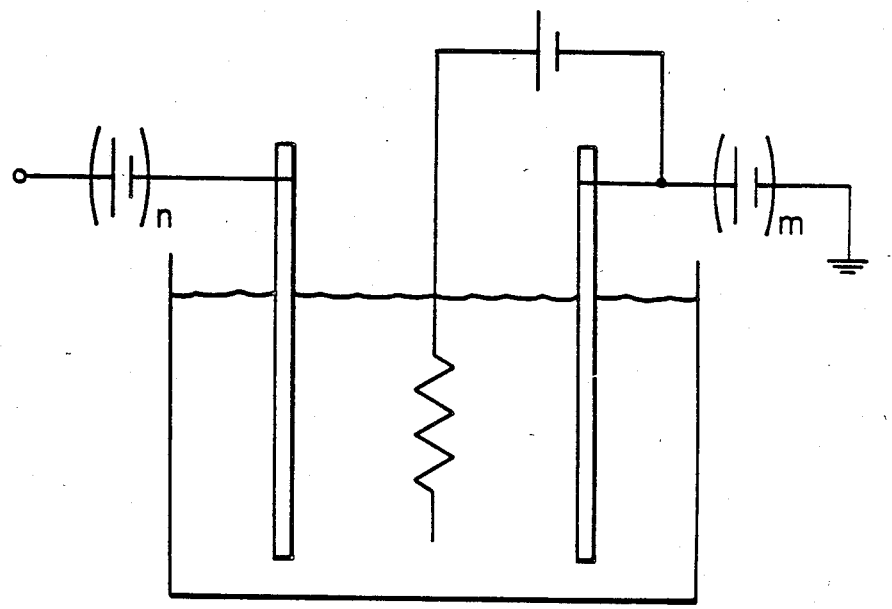
FIG_15B

METHOD AND ARTICLES EMPLOYING ION EXCHANGE MATERIAL

This application is a continuation-in-part of application Ser. No. 932,763 filed Nov. 19, 1986 now abandoned which is a continuation-in-part of application Ser. No. 831,758 filed Feb. 20, 1986 now abandoned, the entire disclosure of each of which is incorporated herein by reference.

The present invention relates to methods and articles employing ion exchange materials, particularly in a cell, especially in an electrolytic as opposed to galvanic cell. Such methods and articles find many uses for example sensing a chosen chemical species (by which we include distinguishing between presence and absence and measurement of concentration), and extraction, concentration or dilution of a chosen species. Thus, the invention has at least two distinct, though related, aspects.

Ion exchange materials are generally solids or gels which contain, or which will react with an ionic material so as to contain, a replaceable ionic species. Cation exchange materials are typically polymers comprising branches containing acidic groups, e.g. —COOH, —SO$_3$H, —PO$_3$H$_2$ and —C$_6$H$_4$OH, and metal (e.g. sodium and copper) salts thereof. Such materials may exchange cations if provided with a suitable electrolyte, generally with no permanent change to the structure of the material. Ionic cation exchange materials are commonly subdivided into "strong acid" and "weak acid" types, which terms refer to the group's acid strength or pK$_a$. Cation exchange materials also include those comprising neutral groups or ligands that bind ions through coordinate rather than ionic bonds. For example, a pyridine group attached to a matrix will form a coordinate bond to Cu$^{2+}$ in CuCl$_2$. Other cation exchange materials include polymers comprising branches comprising complexing or chelating groups, e.g. those derived from aminophosphoric acid, aminocarboxylic acid, and hydroxamic acid.

A second type of ion exchange material is an anion exchange material. Such a material may exchange anions if provided with a suitable electrolyte, again generally with no permanent change to the structure of the material. These materials generally comprise covalently bound, positively charged groups or neutral basic groups which upon protonation become charged. Examples include —NR$_3$A, —NR$_2$HA, —PR$_3$A and —SR$_2$A, where R is an alkyl, aryl or other organic group and A is an anion e.g. halide. A specific example is a bound pyridine group which upon reaction with acid, H$_+$, forms a charged pyridinium group which is then capable of exchanging anions. Anion exchangers consisting of permanently positively charged groups are commonly referred to as "strong base" exchangers, and the sometimes neutral group materials are commonly referred to as "weak base" exchangers.

Ion exchange materials are widely used for extracting ions from liquids, e.g. in water softening and deionization. The extracted ions can be removed and the ion exchange material regenerated, either chemically, using a suitable acid, base, or other regenerant, or electrochemically by a process in which the ion exchange material is separated from the electrodes by cation and anion permselective membranes. See for example U.S. Pat. No. 3,645,884 (Gilliland) and U.S. Pat. No. 4,032,452 (Davis) and an article entitled "Electroregenerated Ion-Exchange Deionization of Drinking Water" by Davis in NTIS PB 270,910 (1977), the disclosure of each of which is incorporated herein by reference.

Other possible uses for ion exchange materials are disclosed in U.S. Pat. No. 4,210,501 (Dempsey et al.) U.S. Pat. No. 4,100,331 (Fletcher et al.) and U.S. Pat. No. 3,297,484 (Niedrach) and an article entitled "Chemical Microstructures on Electrodes" by Faulkner in Chemical and Engineering News, Feb. 27, 1984, the disclosure of each of which is incorporated herein by reference.

We have now discovered that valuable results can be achieved by using ion exchange materials in conjunction with certain types of electrodes, by using them in electrolytic cells, by using them as sensors particularly for locating the presence of an electrolyte, by using them at significant thicknesses on electrodes, by producing them in situ on electrodes, by using them to cover completely certain electrodes, and by employing them in certain sizes and shapes particularly in long lengths.

In a first set of embodiments, the invention is concerned with the extraction from a liquid, or concentration or dilution of a species in a liquid, which liquid in use functions as an electrolyte. Thus, any liquid may be referred to herein as an electrolyte if it has a suitable ionic resistance for the chosen application.

Thus, in one embodiment, the invention provides a method of replacing an ionic species in an ion exchange material containing the ionic species, which method comprises passing a current through a first electrochemical cell which comprises:

(1) a first electrode;
(2) an ion exchange material A which
   (a) contains an ionic species I$_{1A}$, and
   (b) is secured to and in electrical contact with the first electrode at an interface;
(3) a second electrode; and
(4) an electrolyte which electrically connects the first and second electrodes;

and in which cell an electrochemical reaction takes place at the interface between the first electrode and the ion exchange material A and generates an ionic species I$_{2A}$ causes the ionic species I$_{1A}$ to be replaced by a third ionic species.

That other species may be a species I$_{3A}$ present in the electrolyte, which has the same polarity as species I$_{1A}$ and which maintains its polarity at the interface. Species I$_{2A}$ may then have a polarity opposite to that of species I$_{1A}$. A subsequent step may occur in a liquid containing an ionic species I$_{4A}$, namely the replacement of species I$_{3A}$ by I$_{4A}$.

In the case of said subsequent step, the method may additionally comprise the step of passing current through a second electrochemical cell which comprises:

(1) the first electrode, the polarity of the first electrode in the second electrochemical cell being opposite from the polarity of the first electrode in the first electrochemical cell;
(2) the ion exchange material A which contains the species I$_{4A}$ and which is secured to and in electrical contact with the first electrode at the interface;
(3) a further electrode; and
(4) an electrolyte which electrically connects the first and further electrodes, and which, at the interface between the first electrode and the ion exchange material, undergoes an electrochemical reaction which generates an ionic species $I_{5A}$ which causes species $I_{4A}$ to be replaced by another species.

Where the other species is $I_{3A}$ (and said subsequent step is not carried out), the method may comprise the further step of passing the current through a third electrochemical cell which comprises:
  (1) the first electrode, the polarity of the first electrode in the third electrochemical cell being opposite from the polarity of the first electrode in the first electrochemical cell;
  (2) the ion exchange material which contains the species $I_{3A}$ which is secured to and in electrical contact with the first electrode at the interface;
  (3) a further electrode; and
  (4) an electrolyte which electrically connects the first and further electrodes, and which, at the interface between the first electrode and the ion exchange material A, undergoes an electrochemical reaction which generates an ionic species $I_{6A}$ which replaces the ionic species $I_{3A}$.

Such methods can be used to extract species from or release species into a liquid or other electrolyte by means of various electrochemical processes, for example water electrolysis, where a resulting ionic species directly or indirectly effects a modification of the ion exchange material. One purpose of such methods is the purification of the liquid, and another is the recovery of the species. For example industrial wastes, sewage, or mining liquors etc. may be cleaned or salt water may be desalinated. Examples of species that may desirably be recovered include heavy metals, cyanide, phosphates and sodium. Selective ion removal for recovery may be desirable in hydrometallurgical mining operations, metal plating operations and mining of natural waters such as the ocean.

For these methods, the capacity of the ion exchange material may be important, and we prefer that the material have an ion exchange capacity of at least 0.1, particularly at least 0.4 milliequivalents per gram. Preferably the material is in the form of a layer which has a thickness of at least 0.04 mils ($1 \times 10^{-6}$ m), more preferably at least 0.4 mils ($1 \times 10^{-5}$ m), especially at least 4 mils ($1 \times 10^{-4}$ m). However, ion exchange materials may increase substantially in volume between a dry state (in which they are generally manufactured) and a solvated state in which we prefer to use them. It is impossible using prior art techniques to prepare a device comprising an electrode and a layer of an ion exchange material which (a) is less (especially if substantially less) than 100% solvated, (b) is at least 0.04 mils ($1 \times 10^{-6}$ m) thick in the fully solvated state, and (c) is secured to an electrode sufficiently well to make it possible to use it in the methods defined above. As will be explained below, we have solved these problems by using an electrode than can change its dimensions sufficiently to accommodate changes in the dimensions of the ion exchange material, for example as the solvation of the ion exchange material increases. Preferably the electrode comprises a material which electrically and physically contacts the ion exchange material and which has an elastic modulus less than $10^{13}$ dynes/cm$^2$, particularly less than $10^{11}$ dynes/cm$^2$, especially less than $10^{9}$ dynes/cm$^2$. Particularly useful such materials are conductive polymers, i.e. mixtures of a conductive filler and an organic polymer (this term being used to include polysiloxanes), the filler being dispersed in, or otherwise held together by, the organic polymer.

In a second set of embodiments, the invention is concerned with sensing a chosen chemical species. As mentioned above, this includes distinguishing between presence and absence, measurement of concentration, and detecting a change in concentration from some low value to above some threshold value, which change may be several or many decades of increase. In particular the invention provides monitoring by which we include methods which may be left running continuously (including automatic intermittant operation) and methods where testing is carried out from time to time by an operator.

Thus, in a second embodiment the invention provides an apparatus (and corresponding method) for monitoring an electrolyte to determine a change in the concentration of a chemical species in that electrolyte, or for monitoring for the presence of an electrolyte comprising a chemical species, which apparatus comprises:
  (1) a first electrode which is connectable to a source of electric power;
  (2) a second electrode which is connectable to the source of electric power, and which is spaced apart from the first electrode, the first and second electrodes being so positioned and arranged that when a electrolyte is between the electrodes and the source is connected to the electrodes, current passes between the electrodes through the electrolyte; and
  (3) an ion exchange material which
    (a) lies between the first and second electrodes so that when an electrolyte is between the electrodes and current passes between the electrodes, substantially all that current passes through the ion exchange material, and
    (b) has an ionic resistance to the passage of that current which depends upon the concentration of the chemical species in the electrolyte.

The term "depends on" is used herein to include any identifiable variation in resistance with a variation in the concentration of the species.

The resistance between the electrodes depends on the resistance of the ion exchange material, and that appears as a function of the concentration of the chemical species. The resistance between the electrodes as measured by any suitable device will include components due to the resistance of any electrical connections, the resistance of the electrodes, the resistance of the electrolyte outside of the ion exchange material, and the resistance of the ion exchange material itself. We prefer that the resistance of the ion exchange material be large compared to the sum of the other resistances, since then the desired change will result in a greater proportional change in the total resistance. We prefer that the resistance of the ion exchange material is at least 10%, more preferably at least 50%, especially at least 90% of the total. A change in resistance may be measured by applying a constant current and measuring a change in voltage, or by applying a constant voltage and measuring a change in current. In either case, what is being measured is a resistance that obtains at a significant current level.

The technique of the invention has significant advantages over the principal prior art technique for measuring ionic concentrations, that of the pH meter. A pH meter typically comprises a pH responsive glass membrane which in use develops a surface potential which is directly related to the hydrogen ion concentration of its environment.

While a pH meter can accurately measure the concentration of hydrogen ions, it does have some limitations. For example, it can only be used to measure concentrations at discrete points. Also, to remain immediately responsive it must be stored in water when not in use, which means that it cannot be permanently installed if there is not water continuously present. This is a particular problem if it is desired to measure the hydrogen ion concentration at a location that is difficult to access. The pH meter is also easily contaminated, resulting in inaccurate or drifting measurements.

The second embodiment of the invention allows the position of an electrolyte to be determined. In this case, an electrode having a coating of an ion exchange material may be provided in elongate form (like a wire) having a length, say, at least 10, preferably at least 50, more preferably at least 100, times any transverse dimension. The resistance of the electrode in the longitudinal direction is preferably at least $10^3$, more preferably at least $10^4$, especially $10^5$ times its resistance in any transverse direction. Thus the resulting elongate article may be laid for example along the underside of a pipe or other place where electrolyte may leak or otherwise be found. That article may form part of an electrical circuit which is able to respond to a change in resistance of the ion exchange material, and optionally provide information as to where along the elongate article the electrolyte caused the change in resistance.

Thus, the invention also provides an elongate flexible article comprising an elongate conductive core and a coating surrounding and in electrical contact with the core comprising an ion exchange material, and a permeable jacket surrounding the ion exchange material, the article having a length at least 50 times any transverse dimension.

Preferably, the article additionally comprises a second elongate conductive core within the jacket. Such an article, amongst others, may be used to locate an electrolyte by the following inventive method.

Thus, the invention further provides a method for monitoring for the presence of an electrolyte and for locating electrolyte upon its presence, which method comprises providing a system in which, upon the presence of the electrolyte, (1) electrical connection is made between an electrically conductive locating member and an electrically conductive source member;

the locating member and/or the source member comprising an electrode (preferably comprising a conductive polymer), and a coating that electrically surrounds the electrode and which comprises an ion exchange material which has an ionic resistance which depends upon the concentration of a chemical species in the electrolyte;

the connection to the locating member being effective at a first point whose location is defined by the presence of the electrolyte;

the making of the connection enabling the formation of a test circuit which comprises,
(a) the connection,
(b) that part of the locating member which lies between the first point and a second point having a known location on the locating member, and
(c) a power source which causes a current of known size to be transmitted between the first and second points on the location member; and the current and locating member being such that, by measuring the voltage drop between the first and second points, the spatial relationship between the first and second points can be determined;

(2) the voltage drop between the first and second points is measured; and (3) the location of the electrolyte is determined from the measurement made in step (2).

Preferably, the power source is a controlled current source which delivers a known fixed current.

The variation of the resistance of the ion exchange material with concentration of the relevant chemical species preferably occurs as follows. The ion exchange material may be capable of existing in (at least) two forms, such as ionized-nonionized, hydrated-nonhydrated, or as (at least) two different combinations of ion pairs; the position of equilibrium between the two forms will depend on the concentration of the chemical species under test, for example on pH. In turn, the position of equilibrium will result in the material having a characteristic ionic conductivity. The skilled man, on reading the present specification will realize that ionization of bound groups of the ion exchange material (for example by dissociation or addition of $H_+$) will result in hydration of the bound groups. This binding of water molecules may cause the material to swell, and when swollen and permeated with water it may become more ionically conductive.

In order that a change in conductivity of the ion exchange material be manifest as a change in resistance between two electrodes it is preferred that the resistance of the material be high compared to other resistances in series with it (this was addressed above), and also that there be no substantial parallel current paths. Thus, the ion exchange material preferably surrounds an electrode so that if an electrolyte contacts the electrode it does so only after it has passed through the ion exchange material. The material may substantially entirely surround all surfaces of the electrode, or surfaces not surrounded may be insulated from the electrolyte. The ion exchange material may be in direct physical contact with an electrode, or it may be bonded thereto through a layer of an appropriate conductive adhesive. It may, alternatively, merely isolate two electrodes without being in contact with either although that is not at present preferred.

The invention in its second set of embodiments is of particular value as an acid sensor (i.e. for detecting the presence of, or a change in concentration of, hydrogen ions), especially as part of a system disclosed in the following patent specifications, the disclosure of each of which is incorporated herein by reference: EP No. 0,133,748, U.S. Ser. No. 509,897, Masia et al.; U.S. Ser. No. 599,047, Masia et al.; U.S. Ser. No. 599,048, Masia et al.; EP No. 0,144,211, U.S. Ser. No. 566,740, Walsey; U.S Ser. No. 566,829, Walsey; EP No. 0,164,838, U.S. Ser. No. 618,106, Hauptly; U.S. Ser. No. 618,109, Reeder; U.S. Ser. No. 618,108, Brooks et al.; U.S. Ser. No. 608,485, Brooks et al.; EP No. 0,160,441; U.S. Ser. No. 603,484, Frank et al; EP No. 0,191,547; U.S. Ser. No. 691,291, McCoy et al.; U.S. Ser. No. 809,321, McCoy et al.; U.S. Ser. No. 744,170, Stewart et al.; U.S. Ser. No. 787,278, Stewart et al. These specifications together with the present specification will allow the skilled man to design various systems for location of acid or other electrolytes.

In a third set of embodiments there are provided various electrode/ion exchange material combinations, useful for the ion exchange and sensing embodiments described.

Thus, the invention provides an article comprising:
(a) a conductive polymer electrode; and
(b) an ion exchange material in electrical and physical contact with a surface, preferably substantially the entire surface, of the electrode;

the electrode and the material being such that if the article is placed in an electrolyte, substantially all current passing between the electrolyte and the electrode passes through the material.

The invention also provides an article comprising:
(a) an electrode, preferably a conductive polymer electrode; and
(b) an ion exchange material affixed to a surface of the electrode by interpenetration of ion exchange material and electrode material.

The invention also provides an article comprising:
(a) an electrode;
(b) an ion exchange material affixed to a surface of the electrode, the ion exchange material being less than 10% swollen with a liquid; the material being affixed to said surface and the electrode being such that when the ion exchange material is 100% swollen the ion exchange material remains in electrical and physical contact with the electrode.

The invention also provides a bifunctional electrode comprising a laminate of the following layers in the following order:
(a) a cation exchange layer;
(b) a conductive polymer layer (optionally including a metallic core);
(c) a conductive polymer layer (optionally including a metallic core); and
(d) an anion exchange layer.

An electrically insulating layer (optionally ionically porous) may be provided between layers (b) and (c).

The above articles may be made by methods that comprise polymerizing ion exchange precursors in situ on an electrode, especially on a conductive polymer electrode. This allows a strong joint to be achieved, allows interpenetration, allows thick layers of material to be built up, and allows a material to be formed that is unstressed in its swollen state.

Thus, the invention also provides a method of making an article which comprises:
(a) providing an electrode;
(b) contacting the electrode with a liquid ion exchange precursor (preferably monomer); and
(c) polymerizing the precursor, thereby forming an ionically porous layer in engagement with the electrode.

Polymerization in situ of a liquid precursor may be contrasted with a polymerization method that involves a partial polymerization, and application of the resulting gel to an electrode by pressure.

The precursor may have ion exchange functionality, or such functionality may be introduced during or after polymerization.

Where the electrode comprises a thermoplastic material, polymerization is preferably carried out at a temperature above its melt temperature.

The electrode preferably has a surface capable of absorbing ion exchange precursors.

The sensing technique of the invention may be used to monitor the pH and therefore the state of charge of a battery or single cell. A signal produced by a sensor may be used to control some electrical or other device that is to be used in conjunction with the cell. For example, the sensor may control a battery charger to prevent unnecessary charging, it may control a load to prevent excessive discharging, or it may control a battery heater to boost power when the charge is low. Such use, especially control of a charger may be particularly useful in a motor car or other means of transport.

The invention therefore also provides a cell comprising:
(a) an anode;
(b) a cathode;
(c) a sensor;
(d) an electrolyte in contact with said anode, cathode and sensor, said electrolyte containing a chemical species that is involved in an electrochemical reaction that occurs during operation of the cell, said sensor having;
(a) a first electrode,
(b) a second electrode, and
(c) a material positioned with respect to said first and second electrodes such that substantially all current passing between the first and second electrodes passes through said material;

wherein resistance of said material depends on the concentration of said chemical species in the electrolyte.

The invention further provides an electrical system that comprises:
(a) a cell comprising:
(i) an anode,
(ii) a cathode,
(iii) an electrolyte containing a chemical species that is involved in an electrochemical reaction that occurs during operation of the cell, and
(iv) a sensor that can provide a signal responsive to the concentration of said chemical species;
(b) an electrical device that can be electrically connected to the anode and cathode, or a heater; and
(c) control means that controls operation of the electrical device or of the heater in response to a signal from the sensor.

BRIEF DESCRIPTION OF THE DRAWINGS

FIGS. 1 and 2 show a series of electrodes for use in ion exchange;

FIG. 3 shows an alternative arrangement using parallel circuit design;

FIG. 4 shows an arrangement employing a single anode and cathode;

FIG. 5 shows a composite electrode before affixing to anion exchange material;

FIG. 6 shows an electrode together with an ion exchange material;

FIG. 7 shows a first electrode as used for ion sensing;

FIG. 8 shows an alternative first electrode as used for ion sensing;

FIG. 9 shows the electrode of FIG. 7 in combination with a counter, or second, electrode for the detection of hydrogen ions;

FIG. 10 shows a sensor apparatus incorporating the electrode of FIG. 7;

FIG. 11 is a schematic circuit diagram of a circuit incorporating a sensing apparatus of the invention;

FIG. 12 shows a response/regeneration curve;

FIG. 13 shows a battery having a sensor therein;

FIG. 14 shows an electrical system; and

FIG. 15A–15B show further arrangements of a sensor within a battery.

DETAILED DESCRIPTION OF FIRST EMBODIMENTS OF THE INVENTION

The following description relates to the use of the invention for extraction of a species from an electrolyte, or release of a species into an electrolyte. (Description of the invention relating to sensing will follow afterwards.)

It was mentioned above that an electrochemical reaction can take place at an interface between a first electrode and an ion exchange material A, generating an ionic species $I_{2A}$ which causes an ionic species $I_{1A}$ originally present in the material to be replaced by another ionic species.

The species $I_{2A}$ produced by the electrochemical reaction can for example have the same polarity as, and directly replace, the species $I_{1A}$; or it can have the opposite polarity and can extract the species $I_{1A}$ from the ion exchange resin, thus making it possible for a third ionic species $I_{3A}$ contained in the liquid to replace the species $I_{1A}$. In these replacements, and others referred to herein, it is of course possible for ions of the same polarity but different charge to replace each other, with appropriate adjustment of the number of ions. The speed and completeness of the various replacements depends upon the affinity of the ion exchange material for the different ionic species, the relative concentrations of those species, the rates of diffusion and migration of the species in the material and upon any electrochemical forces imposed by an external power source.

The method is particularly efficient when the electrochemical cell further comprises (5) a second ion exchange material B which (a) contains an ionic species $I_{1B}$ and (b) is secured to and in electrical contact with the second electrode at an interface, and an electrochemical reaction takes place at the interface between the second electrode and the ion exchange material and generates an ionic species $I_{2B}$ which causes the species $I_{1A}$ to be replaced by another ionic species. As at the first electrode, the species $I_{2B}$ can directly replace the species $I_{1B}$, or the liquid can contain an ionic species $I_{3B}$ which replaces the species $I_{1B}$.

Set out below are the reactions which take place in a typical direct replacement system in which the liquid is $H_2O$, the first electrode the anode, the ion exchange material A is a polymer containing copper carboxylate groups, $(PCOO)_2Cu$, and the second electrode is not contacted by an ion exchange material.

A. In the Anode region
at the interface

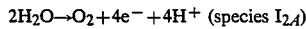
$2H_2O \rightarrow O_2 + 4e^- + 4H^+$ (species $I_{2A}$)

in the ion exchange material

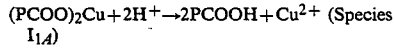
$(PCOO)_2Cu + 2H^+ \rightarrow 2PCOOH + Cu^{2+}$ (Species $I_{1A}$)

B. In the Cathode region
at the interface

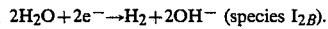
$2H_2O + 2e^- \rightarrow H_2 + 2OH^-$ (species $I_{2B}$).

We have discovered that prior art techniques disclosed in connection with ion-exchange resins are often not suitable for use in the production of articles for use in carrying out the method of the present invention. In particular, we have found problems in delamination of resins from electrodes and have found that such problems can be overcome by in situ polymerization of ion-exchange monomers or other precursors.

Thus, in a second aspect the present invention provides a method of producing an ion-binding article, which comprises:

(a) providing an electrode, preferably comprising a conductive polymer;
(b) contacting the electrode with a monomer or other ion-exchange material precursor; and
(c) polymerizing the precursor, thereby forming a membrane in engagement with the electrode which engagement can preferably resist membrane swelling.

Preferably the ion exchange material is a polymer comprising units having the general formula I;

$$P-R \qquad (I)$$

wherein P is any organic group as a component of a polymer chain, and R is one or more functional groups covalently attached to the polymer chain. In one preferred embodiment R is a cation exchange group. Preferably the cation exchange group is selected from the group consisting of $-SO_3H$, $-COOH$, $-PO_3H_2$, and $-C_6H_5OH$. In another preferred embodiment R is a complexing or chelating group, for example selected from the group consisting of (i) aminophosphoric acids, (ii) aminocarboxylic acids, and (iii) hydroxamic acids, among others. In another preferred embodiment R is an anion exchange group. Preferably the anion exchange group is selected from the group consisting of $-NR_3A$, $-NR_2HA$, $-C_5H_4NHA$, $-PR_3A$, $-SR_2A$, among others.

Preferably the ion exchange material has an ion exchange capacity of at least 0.1 mequiv/g. More preferably it has an ion exchange capacity of 0.5 mequiv/g.

The ion exchange material is preferably coated as a layer of substantially uniform thickness on the electrode. Preferably the layer has a thickness of at least $1 \times 10^{-6}$ m. More preferably it has a thickness in the range $2 \times 10^{-5}$ to $1 \times 10^{-3}$ m, particularly in the range $5 \times 10^{-5}$ to $1 \times 10^{-3}$ m, especially in the range $1 \times 10^{-4}$ to $1 \times 10^{-3}$ m. Preferably the ion exchange material covers substantially the entire surface of the electrode.

The electrodes may comprise any suitable material. The material of each electrode may be the same or different. As example of materials that may be used there may mentioned (i) metals, for example in the form of wires, meshes or sheets, (ii) metal or metal oxide particles for example bonded to a support substrate, (iii) inherently conductive polymers, for example polypyrolles and (iv) conductive polymers. Preferably the electrode in each case comprises a conductive polymer.

A conductive polymer is a mixture of a conductive filler and an organic polymer (this term being used to include polysiloxanes) the filler being dispersed in, or otherwise held together by, the organic polymer. Any suitable conductive filler may be used, for example, carbon black, graphite, metal or metal oxide particles or a mixture thereof. Documents describing conductive polymer compositions and devices comprising them include U.S. Pat. Nos. 2,952,761, 2,978,665, 3,243,753, 3,351,882, 3,571,777, 3,757,086, 3,793,716, 3,823,217, 3,858,144, 3,861,029, 3,950,604, 4,017,715, 4,072,848, 4,085,286, 4,117,312, 4,177,376, 4,177,446, 4,188,276, 4,237,441, 4,242,573, 4,246,468, 4,250,400, 4,252,692, 4,255,698, 4,271,350, 4,272,471, 4,304,987, 4,309,596, 4,309,597, 4,314,230, 4,314,231, 4,315,237, 4,317,027, 4,318,881, 4,327,351, 4,330,704, 4,334,351, 4,352,083, 4,388,607, 4,398,084, 4,413,301, 4,425,397, 4,426,339, 4,426,633, 4,427,877, 4,435,639, 4,429,216, 4,442,139, 4,459,473, 4,481,498, 4,476,450, and 4,502,929; J. Applied Polymer Science 19, 813–815 (1975), Klason and Kubat; Polymer Engineering and Science 18, 649–653 (1978), Narkis et al; and commonly assigned U.S. Ser. Nos. 601,424 now abandoned, published as German OLS No. 1,634,999; 732,792 (Van Konynenburg et al), now abandoned, published as German OLS No. 2,746,602; 798,154 (Horsma et al), now abandoned, published as German OLS No. 2,821,799; 134,354 (Lutz); 141,984 (Gotcher et al), published as European Application No. 38,718; 141,988 (Fouts et al), published as European Application No. 38,718, 141,989 (Evans), published as European Application No. 38,713, 141,991 (Fouts et al), published as European Application No. 38,714, 150,909 (Sopory), published as UK Application No. 2,076,106A, 184,647 (Lutz), 250,491 (Jacobs et al) published as European Application No. 63,440, 272,854 and 403,203 (Stewart et al), published as European Patent Application No. 67,679, 274,010 (Walty et al), 300,709 and 423,589 (Van Konynenburg et al), published as European Application No. 74,281, 369,309 (Midgley et al), 483,633 (Wasley), 493,445 (Chazan et al), published as European Patent Application No. 128,664, 606,033, (Leary et al), published as European Application No. 119,807, 509,897 and 598,048 (Masia et al) published as European Application No. 84,304,502.2, 524,482 (Tomlinson et al) published as European Application No. 84,305,584.7, 534,913 (McKinley), 535,449 (Cheng et al) published as European Application No. 84,306,456.9, 552,649 (Jensen et al) published as European Application No. 84,307,984.9, 573,099 (Batliwalla et al) and 904,736, published as UK Patent Nos. 1,470,502 and 1,470,503, and commonly assigned applications Ser. Nos. 650,918 (Batliwalla et al, MP0959), 650,920 (Batliwalla et al, MP0961-US1), continuation-in-part 663,014 (Batliwalla et al, MP0961-US2), continuation-in-part 735,408 (Batliwall et al, MP0961-US3), 650,919 (Batliwalla et al, MP0962), 650,921 (Kheder, MP0973), 711,790 (Carlomagno, MP0991), 667,799 (Frank, MP0998), 711,908 (Ratell, MP1016), 711,907 (Ratell, MP1021), 711,909 (Deep et al, MP1022), 720,118 (Soni et al, MP1039), and 711,910 (Au et al, MP1044). The disclosure of each of the patents, publications and applications referred to above is incorporated herein by reference.

In one embodiment the electrode comprises a conductive polymer, and the ion exchange material comprises a polymeric material which has been bonded to the electrode surface in such a manner that there is produced a layer of a polymer blend between electrode and material which is at least 1 optionally at least 5 microns thick. The polymer blend layer is a blend of the polymer of the ion exchange material or the ion exchange material precursor, and the conductive polymer of the electrode.

The electrodes may be any shape. In a preferred embodiment the electrodes are planar. In another preferred embodiment the electrodes are cylindrical.

Preferably the electrode has an elastic modulus less than $10^{13}$ dynes/cm$^2$, and it is preferably solid in cross-section.

A particularly preferred embodiment of the invention when used for ion removal comprises a plurality of electrodes, preferably planar, which are arranged in a stack, that is with each face of an electrode facing a face of its adjacent electrode. In the stack each electrode is preferably a bipolar electrode, that is one of its faces behaves as an anode and the other of its faces behaves as a cathode. With this arrangement each adjacent pair of electrodes functions as a cell which can effect ion extraction and expulsion. Thus for a stack of bipolar plates the capacity for ion exchange and expulsion is approximately n×capacity of a single anode/cathode cell.

Referring now to the drawings, FIGS. 1 and 2 show a stack of electrodes 2 supported in a casing 4 by insulating supports 6. Each electrode is planar and is arranged substantially parallel to its neighbor. The outermost electrodes (that is those nearest to the casing sides) are connected to a DC power source 8. As illustrated in FIG. 1 the electrode on the right of the drawing is connected to the negative terminal of the power source, and the electrode on the left of the drawing is connected to the positive terminal of the power source. A liquid 10 containing an ionic component (MA) is recycled through the casing as shown by the arrows. The inlet and outlet for the liquid 10 are at opposite ends of the casing 4. Thus the liquid 10 passes over each electrode 2. The liquid 10 contains a number of ionic species. From the liquid, cation M$^+$ and anion A$^-$ are to be extracted.

Each electrode 2 is a bipolar electrode, that is one of its surfaces behaves as an anode (oxidation occurs at its surface), and the other of its surfaces behaves as a cathode (reduction occurs at its surface). Each electrode comprises a conductive polymer core, which may include a metallic current collector. The outermost electrodes are coated on their inward facing surfaces with an ion exchange material. The central electrodes are coated on both their surfaces with an ion exchange material. All those surfaces facing one direction (to the left as illustrated) are coated with a weak acid cation exchange material PCOOH 12, (in which the exchangeable ion is H$_+$). All those surfaces facing in the opposite direction (to the right as illustrated) are coated with a weak base anion exchange material PNR$_2$ 14. The cation exchange material PCOOH has a greater affinity for M$^+$ than for any of the other cations in solution 10. It also has a greater affinity for H$_+$ ions than for M$^+$ ions. The weak base anion exchange material has a greater affinity for OH$^-$ ions than for A$^-$ ions. With the power source connected as shown, the left facing surface of each electrode behaves as a cathode, and the right facing surface of each electrode behaves as an anode. Thus a series current passes between the outermost electrodes. As current is passed the following reactions occur at each anode and cathode surface, and in the ion exchange materials.

Cathode

$$2H_2O + 2e^- \rightarrow 2OH^- + H_2 \tag{A}$$

In cation exchange material 12 at the cathode

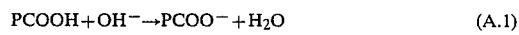
$$PCOOH + OH^- \rightarrow PCOO^- + H_2O \tag{A.1}$$

$$PCOO^- + M^+ \rightarrow PCOOM \tag{A.2}$$

Anode

$$2H_2O \rightarrow 4H^+ + O_2 + 4e^- \tag{B}$$

In anion exchange material 14 at the anode

$$PNR_2 + H^+ + A^- \rightarrow PNR_2HA \tag{B.1}$$

Thus ions $M^+$ and $A^-$ are extracted from liquid 10.

The extracted ions $M^+$ and $A^-$ may then be expelled into a liquid. To do this the liquid 10 may be replaced by pure water, and the electrical connections to the power source reversed. With the reversed connections each surface coated with a cation exchange material now behaves as an anode, and each surface coated with an anion exchange resin now behaves as a cathode. As current is passed the following reactions occur at each cathode and anode surface.

Anode $$2H_2O \rightarrow 4H^+ + O_2 + 4e^- \tag{C}$$

In cation exchange material at the anode $$PCOOM + H^+ \rightarrow PCOOH + M^+ \tag{C.1}$$

Cathode $$2H_2O + 2e^- \rightarrow 2OH^- + H_2 \tag{D}$$

In anion exchange material at the cathode $$PNR_2HA + OH^- \rightarrow PNR_2 + H_2O + A^- \tag{D.1}$$

Thus ions $M^+$ and $A^-$ are expelled into the new solution. Because the cation exchange material has a greater affinity for $H^+$ ions than $M^+$ ions reaction C.1 above is strongly biased in the forward direction. Similarly, reaction D.1 is strongly biased in the forward direction. Thus the explusion or "elution" of MA is very efficient.

Ion exchange is more efficient than previous methods employing chemical or electrical regeneration because all $H^+$ and $OH^-$ "eluant" must pass through the ion exchange layer bonded to the electrode. In contrast, the passage of eluant through any system using ion exchange resin beads, as in the prior art, leaves open the possibility that eluant ions will bypass many beads. This is a particular possibility when the ion exchange material exhibits a large ionic resistance, for example when the beads do not swell considerably. The present invention (unlike some of the prior art systems employing electrochemical regeneration, e.g. U.S. Pat. No. 4,032,452, Davies) can allow the use of ion exchange layers and solutions of a broader range of resistivities. The present invention in particular can allow the use of low or high resistivity solutions regardless of the resistivity of the ion exchange layer. When compared to chemical regeneration, the methods of regeneration disclosed herein benefit from the economy, safety, cleanliness and convenience achievable with electrical regeneration.

The $M^+$ ions can be extracted from liquid 10, using the apparatus shown in FIG. 1, by an alternative method. In that alternative method liquid 10 is preceded by another ionic solution, for example a sodium chloride (NaCl) solution, and the apparatus electrically powered as shown. Reactions corresponding to (A) and (B) occur in a sodium chloride solution such that the ion exchange material becomes PCOONa and the anion exchange material becomes $PNR_2HCl$. Then the sodium chloride solution is replaced by liquid 10 containing the $M^+$ and $A^-$ ions, with power source 8 disconnected. Since the cation exchange material $PCOO^-$ has a greater affinity for $M^+$ than for $Na^+$ ions, the following passive exchange reaction occurs spontaneously:

$$PCOONa + MA \rightarrow PCOOM + NaA$$

The extracted $M^+$ ions are then expelled into solution in the manner described above.

The alternative method is particularly preferred where the cationic species to be extracted is one which is liable to be reduced to a metal or precipitate at the cathode surface during the powered extraction process.

FIG. 3 shows an alternative arrangement illustrating a parallel circuit design. Each bifunctional electrode 30 is substantially planar and comprises five layers. The five layers are from left to right, cation exchange layer 32, conductive polymer 34, insulating core 36, conductive polymer 34, and anion exchange layer 38. Each conductive polymer layer is connected to a power supply 8. The conductive polymer layer may include a metallic current collector. As in the series circuit, each electrode is arranged such that all the surfaces facing in one direction behave as anodes and all the surfaces facing in the other direction behave as cathodes. Liquid 10 is fed into the casing 4 as in the embodiment illustrated in FIGS. 1 and 2. Thus a series of parallel electrochemical cells are produced. Equivalent extraction and expulsion processes to those described with reference to FIGS. 1 and 2 can be carried out.

FIG. 4 shows an alternative device in which there is only one anode and cathode, or all anodes and cathodes form a single structure. A layered strip is prepared. The strip comprises four elements (1) a conductive polymer electrode 42 coated on one surface with an anion exchange material, (2) a mesh spacer 44, and (3) another conductive polymer electrode 46 coated on one surface with a cation exchange material, and (4) an insulating layer shown in dotted outline, 48. The conductive polymer electrodes are positioned so that the ion exchange material coatings face each other and are separated by the mesh spacer. The strip is sealed at its edges and ends, and a solution (from which ions are to be extracted, or into which ions are to be expelled) is fed into the strip between the ion exchange materials, for example into the porous end-piece 49. The conductive polymer layers comprising current collectors are connected to the terminal of a power supply so that one behaves as an anode and the other as a cathode. Extraction and expulsion reactions equivalent to those described with reference to FIGS. 1 to 3 occur at the cathode and anode surfaces. The ion exchange occurs along the length of the strip. The strip is spiralled so that it is a convenient shape and size, and the insulating layer prevents shorting between the two electrodes.

A preferred method will now be described of making an ion-binding article, suitable for use in the method of replacing an ionic species described above. This preferred method allows an ion-exchange material to be attached to an electrode sufficiently securely that swelling forces, resulting for example from the immersion of a dry or less than 100% solvated article in a solution, for example an aqueous solution, may be resisted. In general, one or more monomers or other ion-binding resin precursors are polymerized in situ, i.e. in contact with an electrode. The precursor may have ion-exchange functionality before it is brought in contact with the electrode, functionality may be introduced during polymerization, or functionality may be introduced after polymerization is complete.

It is preferred that the electrode in contact with monomers or other precursors be capable of absorbing one or more of the precursors. It is also preferred that the electrode comprise a thermoplastic material, for example a conductive polymer, especially a polymer having carbon black therein. Absorption of the precursor, we have found, can result in a bond between the electrode and the resulting ion-exchange resin that is surprisingly strong. It is believed that this bond has the nature of an interpenetrating network. The bond region may penetrate the surface of the electrode to a distance from, say, $10^{-7}$ to $10^{-3}$ m, preferably $10^{-7}$ to $1 \times 10^{-4}$ m. The depth achieved in practice will depend on the solubility of the precursor in the electrode material, and on the temperature at which polymerization is carried out. Thus, the temperature, the precursor and electrode materials (and thus the solubility of one in the other) may be varied to achieve the desired depth of interpenetration, and thus the desired bond strength.

Two examples may be given. Firstly, an electrode comprising a composite of metal wire and SCLAIR 11W plus carbon was penetrated to a depth of about $5 \times 10^{-5}$ m by a polymerizing liquid monomer polymerized at a temperature 20° C. above the $T_m$ (melt temperature) of the electrode composite. Secondly, a depth of penetration of about $1 \times 10^{-4}$ m was achieved in the case of an Elvax 360/carbon electrode composite and a liquid monomer polymerized at 40° C. above $T_m$.

Successful results can be obtained where the polymerization temperature is below $T_m$, but the bond depth is likely to be small. At such lower temperatures, the solubility of the precursor in electrode material becomes more important.

Examples of methods of preparing ion-binding electrode articles may now be given to illustrate the three possibilities, mentioned above, as to when ion-exchange functionality is introduced.

Which route is chosen for the introduction of functionality will, of course, depend on the functional group desired and on the chemical nature of the electrode and polymer backbone of the ion-exchange resin, and on any solvent employed. It may, also, however, depend on other behavior of the various chemical species, for example on the solubilities of the species in a common solvent such as a coating solution, and upon the solubility of the various possible precursors in the electrode material.

In many cases, it may be desirable to carry out the polymerization or the introduction of functionality in a different solvent from that in which the final ion-binding article will be used. For example, a solvent such as methyl ethyl ketone may be used for reactions such as the production of fully quaternized resins, whereas the final product may be used in aqueous solution. Swelling in non-aqueous solvents, and exchange of one solvent for another during preparation of these articles is likely to put considerable stress on the bond between the ion-exchange material and the electrode. The strong engagement with the electrode that we are able to achieve through absorption and in situ polymerization, particularly of monomer precursors, is advantageous in this respect.

Embodiments of the invention will now be described in the following examples.

EXAMPLE 1

An electrode 56 before bonding to an ion exchange membrane, is 3.3 cm wide, 6.0 cm long and 0.3 cm thick. It is illustrated in FIG. 5 and it consists of three materials, a conductive polymer blend of 41.8% graphite (GP-39, trade mark), 12.6% carbon (Conductex 975, trade mark), and 43.5% base polymer 51 and 52, an aluminum mesh current collector 53, and unfilled base polymer for insulation 54 and 55. The insulating material is positioned such that only one face of conductive polymer 51, the active electrode surface, is exposed upon immersion in a liquid, and the current collector is placed between the conductive polymer face opposite the exposed face and the insulating layer. The aluminum mesh and insulating layer extend above the active electrode surface 51 to conductive polymer 52 to provide a place for the electrical connection.

The conductive polymers 51 and 52 are both in electrical contact with aluminum mesh 53 and are separated by a 1 cm wide insulating polymer strip 55.

The ion exchange material may be deposited in one step by employing a monomer possessing the desired ion exchange functionality. Electrode 56 was heated on a hot plate to 135° C. for 3 min. and 0.25 g of a solution of 47.43 weight percent 2-ethylhexyl acrylate, 45.90% 4-vinylpyridine, 3.49% technical divinylbenzene (55% grade), and 3.18% t-butylperoctoate added dropwise to cover the surface of the exposed face of the conductive polymer. The electrode was then covered with a shallow dish to contain vapors and left at 135° C. for 10 min., when it was removed and allowed to cool. This was swollen in 1 M HCl to form the pyridinium chloride form of the ion exchange material.

EXAMPLE 2

Rather than using a functional monomer as in Example 1, the ion exchange functionality may be incorporated during the polymerization. Electrode 56 was heated to 120° C. on a hot plate for 3 min., and 0.56 g of a solution of 37.75 weight % vinylbenzylchloride, 7.5% 4-vinylpyridine, 4.2% technical divinylbenzene, 1.3% t-butylperoctoate, and 50% 1-methylnapthalene (an inert diluent) added dropwise to cover the surface of the exposed face of the conductive polymer. The electrode was then covered with a shallow dish to contain vapors and left at 120° C. for 6 min., when it was removed and allowed to cool. After soaking the article for 24 hours first in 50/50 methylethyl ketone/methanol then in water, the article could be placed in 1 M HCl to form the pyridinium chloride form of the ion exchange material.

EXAMPLE 3

This article was prepared as in Example 2 but a monomer solution of 30.66 weight percent 4-vinylpyridine, 12.86% vinylbenzyl chloride, 5.0% technical divinylbenzene, 1.48% t-butylperoctoate, and 50% 1-methylnapthalene was added dropwise to the electrode 56 heated to 120° C.

EXAMPLE 4

A hydrophobic layer containing an ion exchange precursor may be attached to electrode 56 as described in Example 1, and subsequently reacted in one or more steps to introduce the ion exchange group. In this example a two step functionalization process is required to produce a water swellable ion exchange layer with high capacity for copper ion. Electrode 56 was heated to 135° C. on a hot plate for 3 min. and 0.25 g of a solution of 91.4 weight percent vinylbenzyl chloride, 6.2% technical divinylbenzene, and 2.4% t-butylperoctoate added dropwise to cover the exposed face of the conductive polymer This was covered with a shallow dish to contain vapors, left at 135° C. for 10 min., and allowed to cool. The weight of the ion exchange precursor layer was determined gravimetrically, and found to be 0.20 g.

Twenty percent quaternization, based on vinylbenzyl chloride, was introduced by using enough dimethylethylamine to react wtih 30% of the vinylbenzyl chloride groups (one-third of this reagent does not react). This functionality is required to provide adequate water swellability and to allow the introduction of sufficient sarcosine functionality in the following step. The article with a 0.20 g layer (possessing 0.18 g vinylbenzyl chloride) was therefore swollen in a mixture of 200 ml methylethyl ketone and 0.026 g dimethlethylamine for 2 hours then heated at 40° C. for 16 hours. After stirring in water several hours the article could be treated with 1 M KBr to exchange bromide for chloride. The relative intensities of the bromide and chloride peaks in an X-ray fluorescence spectrogram confirmed that 20% of the vinylbenzyl chloride groups had been quaternized.

The 20% quaternized article, with or without the KBr exchange step, was functionalized with sarcosine by placing it in a solution of 18.3 g sodium sarcosinate, 180 ml methanol and 120 ml water, stirring 2 hours, and then heating at reflux for 16 hours. After cooling to room temperature, 165 ml. of 1 M HCl was added slowly, and the article rinsed in water. The copper capacity of this ion exchange layer was measured by stirring in 1 M $CuCl_2$ for 2 hours, rinsing for 2 hours, and finally extracting the copper in 1 M HCl. The absorbence of the HCl solution at 788 nm was used to calculate the copper ion concentration with Beer's law (using an extinction coefficient of 11.4), and this article was found to have a copper capacity of 0.76 mmoles Cu/g ion exchange layer (based on an ion exchange precursor layer weight of 0.20 g.).

EXAMPLE 5

This is a further example of introduction of the sarcosine ion exchange functionality following the polymerization of the monomers. The article from Example 2 (without the HCl treatment) was placed in a solution of 18.3 g sodium sarcosinate, 180 ml. methanol and 120 ml. water, stirred for 2 hours at room temperature, then heated at reflux for 16 hours. The mixture was cooled to room temperature, 165 ml. of 1 M HCl added slowly, and the article rinsed in water for 16 hrs. After stirring in 1 M KOH for 2 hours, water for 2 hours, 1 M $CuCl_2$ for 2 hours, and finally water for 2 hours, the copper ion capacity was measured by extraction of the article with 1 M HCl and measurement of the solution absorbance using visible spectroscopy. The copper capacity was found to be 0.90 mmoles Cu/g ion exchange material.

EXAMPLE 6

FIG. 6 shows a first electrode 62 as described in Example 4 with the sarcosine ion exchange layer 63 in the copper form placed in a 3.5 cm wide by 5.5 cm high by 1.3 cm wide plexiglass cell 64 facing a second electrode 66 without an ion exchange layer, and 11.0 ml 0.1 F $NaClO_4$ liquid electrolyte added immediately to level 67 just above the top of layer 63. Powered expulsion of copper(II) (0.76 mmole copper (11) per gram) was effected by connecting the two electrodes through silver painted conductive polymer tabs 68 to a constant current power supply 69 with the first electrode 62 as the anode. A current of 1 mA/$cm^2$ (6 mA total) was applied for 80 minutes, passing a total of 1.5 mmole electrons/g ion exchange layer and providing 1.5 mmole $H^+$/g via the electrochemical oxidation of water (Two $H^+$ are required for each copper(II) originally in the ion exchange layer.) The direct electrochemical expulsion of Cu(II) is represented by the following reactions:

  (a)

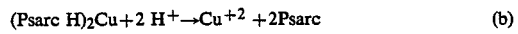  (b)

Psarc in reaction b represents the sacosine functionalized ion exchange layer. A light blue $Cu(OH)_2$ precipitate forms during the expulsion. The power supply was disconnected and the cell left to rest for one hour. The electrodes 62,66 were removed and the quantity of copper expelled calculated directly from the copper found as $Cu(OH)_2$ precipitate, and by difference after measuring the copper remaining in the ion exchange material on electrode 62. The $Cu(OH)_2$ solid was dissolved by adding 1.0 ml 1.0 M aqueous HCl, and the copper concentration measured by visible spectroscopy. The copper remaining in the ion exchange layer after expulsion was measured as before for the capacity measurement by extraction with 1.0 M HCl.

For this example both measurements found the efficiency of copper(II) expulsion to be 20%, defining this quantity as 100×(2×moles copper expelled/moles electrons passed).

EXAMPLE 7

The electrode article prepared in Example 5, with the copper sarcosinate ion exchange material (the first electrode 62) and the article prepared in Example 3, with the pyridinium chloride material (the second electrode 66) were placed in the plexiglass cell 64 of FIG. 6, again with the active electrode surfaces 51 facing each other, and 11.0 ml 0.1F $NaClO_4$ liquid electrolyte added immediately. Powered expulsion was effected by connecting the first electrode 62 in the copper form to the positive terminal of a constant current power supply 69, and the second electrode 66 in the proton form to the negative terminal. A current of 1 mA/$cm^2$ (6 mA total) was applied for 96 minutes, passing a total of 1.8 mmole electrons/g ion exchange material and providing 1.8 mmole $H^+$/g to the first electrode 62 (2$H^+$ are required for each Cu(II)). The direct Cu(II) and 1.8 mmole $OH^-$/g to the second electrode 68 expulsion at the first electrode is as described in Example 6. The indirect chloride expulsion at the second electrode is represented as follows:

$2H_2O + 2e^- \rightarrow 2O^- + H_2$  (c)

  (d)

$P_{py}$ in reaction d represents the pyridine (py) functionalized ion exchange layer. The copper(II) was expelled into the liquid as soluble $CuCl_2$ rather than the solid $Cu(OH)_2$ in Example 1 because the $OH^-$ produced via water reduction at the second electrode 66 in reaction C reacts with the pyridinium chloride group of the second ion exchange layer. The cell was disconnected and left to rest for one hour, and the quantity of expelled copper(II) measured as in Example 6. The efficiency of copper(II) expulsion in this experiment was 98%.

DETAILED DESCRIPTION OF SECOND EMBODIMENTS OF THE INVENTION

The following description relates to sensing a chosen chemical species and to control of operation of a battery or single cell. A sensor may comprise first and second electrodes to which a power source is connected, and an ion exchange material attached to at least one of the electrodes, or otherwise separating them. The sensor will in general, therefore, function as an electrolytic cell.

When a power source is connected to the electrodes of the sensor cell, a current flows between the electrodes, the magnitude of the current depending on (as hereinbefore defined) the concentration of the chemical species in the liquid. In one embodiment, using a particular ion exchange material, in the substantial absence of the chemical species a nominal or trickle current flows, of the order of $10^{-8}$ A/cm$^2$, and in the presence of chemical species in concentrations of $10^{-3}$ M (the threshold value) or greater a significant current flows, of the order of $10^{-4}$ A/cm$^2$. These current and threshold concentration quantities depend at least in part on the ion exchange material employed, and may vary by many orders of magnitude when using alternative ion exchange materials. The change in the current flow is explained as follows. When the ion exchange material is in the presence of the chemical species it exhibits a lower ionic resistance. At each electrode surface an electrochemical reaction takes place, electrons being provided for chemical reduction at the cathode and consumed in chemical oxidations at the anode. Thus, in the presence of a sufficient concentration of chemical species, that is a concentration exceeding the threshold value, a more active electrochemical cell is formed, and a larger electrical current flows between the electrodes. The speed with which the cell current increases depends upon the concentration of the chemical species, that is upon the degree to which the concentration exceeds the threshold level, $10^{31\ 3}$ M in this example. Thus the cell current increases faster for greater chemical species' concentrations. In this example, for a concentration of $10^{-1}$ M, the cell requires an hour before passing $10^{-4}$ A/cm$^2$, and for concentration of 3M, requires 2 minutes to reach this same current density. In contrast, in the absence of the chemical species the ion exchange material exhibits a greater ionic resistance. Thus a less active electrochemical cell is formed and a smaller, or only a trickle, electrical current flows between the electrodes.

The first and second electrodes may comprise any suitable conductive material. The two electrodes may comprise the same or different materials. As example of materials that may be used there may mentioned (i) metals, for example in the form of wires, meshes or sheets, (ii) metal or metal oxide particles for example bonded to a support substrate, (iii) intrinsically conductive polymers, for example polypyrolles, and (iv) conductive polymers. Preferably one or both electrodes in each case comprises a conductive polymer which forms at least part of the surface of the electrode.

The electrodes may be any shape. The two electrodes may be the same shape or a different shape. In one preferred embodiment one, or preferably both, electrode is elongate, for example in the form of a wire. In another embodiment the, or each, electrode is substantially planar, for example in the form of a flat plate.

The ion exchange material is arranged so that substantially all current passing through the electrochemical cell passes through the ion exchange material. The preferred positioning of the ion exchange material required to achieve this result depends inter alia on the shape of the electrode. For an electrode in the shape of a wire, the ion exchange material preferably covers the entire curved surface of the wire, in order completely to separate the electrode from the chemical species. For an electrode in the shape of a flat plate, the ion exchange material is preferably bonded to one or to both of the flat surfaces of the electrode, depending on how the electrode is to be exposed to the liquid. If the liquid forms one wall of a bath containing the electrolyte only one surface (the inner facing surface) need be covered. If the electrode is immersed in the bath, preferably both surfaces are covered, at least to be the electrolyte level.

In preferred embodiments when the ion exchange material is exposed to the chemical species it swells by absorbing some or all components of the liquid. In this case the first electrode is preferably extensible so that it can comply with that swelling. The term "comply" is used herein to mean that the electrode can extend such that the bond between the electrode and the ion exchange material is not damaged by the swelling. Preferably the peel strengths of the bond between the electrode and the ion exchange material when the ion exchange material is in its pre-swollen and swollen state are equal to, or exceed, the tensile strength of the electrode itself. For this reason inter alia it is preferred to use conductive polymers for the electrodes since those polymers typically can be extended without adversely effecting their electrical properties. In preferred embodiments the liquid used is aqueous.

Preferably the ion exchange material is provided as a layer. The layer preferably has a minimum thickness of 1 micron, preferably 20, more preferably 50, especially 100 microns. The preferred maximum thickness may be 1000 microns or more. More preferably the thickness is in the range 50 microns to 1000 microns, typically 50–300 microns.

For some applications, the ion exchange material is preferably crosslinked. Crosslinking may be effected by chemical means, or by irradiation, for example with a beam of fast electrons or gamma rays. Crosslinking 0.2–20 mol %, especially 0.5–6 mol %, is preferred.

The electrode is preferably flexible by which is meant that at 23° C. it can be wrapped around a 4 inch (10 cm) mandrel, preferably 1 inch (2.5 cm) mandrel, without damage.

The ion exchange material may comprise any suitable polymer which on exposure to the chemical species changes, preferably decreases, its electrical resistance. Preferably the ion exchange material comprises a polymer comprising a plurality of repeating units having the general formula I $$P\text{—}R \qquad (I)$$

wherein P is an organic polymer group, and R is a functional group which renders the ion exchange material more ionically conductive in the presence of the chemical species. R is typically a neutral functional group in the less conductive state, and a charged group in the more conductive state. The polymer may be a branched or straight-chain polymer selected from the group comprising a homopolymer, a copolymer, a terpolymer and a blend of such polymers.

Preferred embodiments of the invention can be used to detect changes in concentration of hydrogen ions, i.e. acid. In these cases the first electrode may be made either the cathode or the anode in the electrochemical sensor cell. Certain advantages are achieved when the first electrode is made the cathode, and other advantages are achieved when the first electrode is made the anode. In one embodiment, for an acid sensor, in the absence of a sufficient concentration of hydrogen ions the ion exchange material has a low ionic conductivity, passing only $10^{-8}$ A/cm². After the ion exchange material has contacted hydrogen ions, $10^{-3}$ M or greater in this example, it becomes much more conductive, passing $10^4$ A/cm². Thus when an aqueous liquid containing a sufficient hydrogen ion concentration is introduced between the electrodes a more active electrochemical sensor cell is formed (i.e. a greater current passes between the electrodes).

As an example of the invention, the electrochemical reactions which typically occur at the cathode and anode surfaces, giving rise to passage of the electrical current, are given for an acid sensor in an aqueous liquid, the first electrode is the cathode and the second electrode is the anode.

Cathode: $2H_2O + 2e^- \rightarrow 2H^- + H_2(s)$ ( 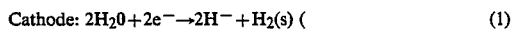  (1)

Anode: $2H_2O \rightarrow 4e^- 4H^+ + O_2(g)$ 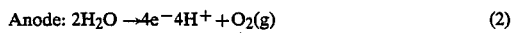  (2)

A larger electrical current flows between the electrodes in the presence of hydrogen ions as a result of the layer's ionic resistance decreasing. Typically the total measured current is of the order of $10^{-5}$ to $10^{-3}$ A. Depending on the materials used, the sensor cell may indicate simply whether the pH is above or below a certain value, or it may be able to give quantitative information over a range of pH values.

For detecting the presence of hydrogen ions, it is preferred that the ion exchange material comprises basic functional groups R which upon reaction with hydrogen ions causes a decrease in the ionic resistance of the ion exchange material. This functional group R is typically a neutral basic group which becomes charged upon reaction with a hydrogen ion. More particularly it may be selected from the family of nitrogen containing bases. These may be primary, secondary, or tertiary alkyl or aryl substituted amines, substituted and unsubstituted nitrogen containing heterocylics, amides, or any other group which causes the ion exchange material to become more ionically conductive in the presence of hydrogen ions. For detecting the presence of an acid, the ion exchange material preferably has an acid dissociation factor $pK_a$ in the range 0 to 6. It is this quantity which determines the threshold value mentioned earlier. A smaller $pK_a$ material requires a greater concentration of acid for detection.

In one preferred embodiment for use with aqueous liquids the ion exchange material comprises pyridine ($-C_5H_4N$) as the functional group R. That polymer becomes more ionically conductive in the presence of hydrogen ions as a result of the following reaction:

$$P—C_5H_4N + H^+ \rightarrow P—C_5H_4NH^+$$

The formation of the pyridinium group ($P—C_5H_4NH^+$) is accompanied by swelling of the polymer, due to absorption of water.

Other preferred embodiments of the invention can be used to detect the presence of chemical bases (e.g. hydroxide, ammonia, carbonate). In these cases the first electrode may be made either the anode or the cathode, there being different advantages to each arrangement. After the ion exchange material has contacted the basic solution, it becomes more ionically conductive. Thus when a basic aqueous solution containing hydroxide ions, for example, is introduced between the electrodes, the ionic resistance of the ion exchange material decreases and a more active electrochemical cell is formed. For a base sensor in which the first electrode is made the anode and the second electrode the cathode, reactions (1) and (2) above typically take place at the cathode and anode surface as in the case of the acid sensor. Thus upon exposure to hydroxide ions the current passed between the electrodes increases. Typically that measured current is of the order of $10^{-5}$ to $10^{-3}$ A.

For detecting the presence of basic solutions, it is preferred that the polymer coating comprises acidic functional groups R which upon reaction with a base causes the ion exchange material to become more ionically conductive. This functional group is typically a neutral acidic group which becomes charged upon reaction with chemical bases. More particularly it may be selected from the families of carboxlic acids, diketones, oximes, phenols, or any other group which causes the ion exchange material to become more conductive in the presence of hydroxide ions. For detecting the presence of a base, the ion exchange material preferably has a dissociation factor $pK_a$ of 8 to 14. In this case a greater $pK_a$ material requires a larger concentration of base for detection.

In one embodiment the ion exchange material comprises carboxylic acid as the functional group R. The carboxylic acid groups cause the ion exchange material, P—COOH, to become more conductive in the presence of basic solutions as follows, using hydroxide as an example:

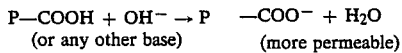

P—COOH + OH⁻ → P   —COO⁻ + H₂O
(or any other base)      (more permeable)

When the relevant chemical species from the liquid contacts the first electrode, generally after being absorbed by and after passing through the ion exchange material, it may undergo an electrochemical reaction at the electrode surface. Another chemical species will undergo another chemical reaction at the second electrode surface, thus allowing the passage of current. In preferred embodiments for detecting hydrogen ions in an aqueous liquid, when water contacts the first electrode as a cathode it reacts to produce hydroxide ions (Reaction (1)). Similarly in a preferred embodiment for detecting basic solutions in aqueous solution, when water contacts the first electrode as an anode it reacts to produce hydrogen ions (Reaction (2)). Preferably the ion exchange material is positioned at that electrode where the products of the electrochemical reaction are those which will drive the ion exchange material back to its less conductive state. For example, for the detection of hydrogen ions when the ion exchange material comprises a polymer comprising units having the general formula P—$C_5H_4N$, the ion exchange material should be positioned at the cathode. The reactions that take place are as follows:

$$P—C_5H_4N + H^+ \rightarrow P—C_5H_4NH^+ \quad (3)$$

At cathode: $2H_2O + 2e^- \rightarrow 2OH^- + H_2(g)$ (4)

$P-C_5H_4NH^+ + OH^- \rightarrow P-C_5H_4N + H_2O$ (5)

Similarly for the detection of basic solutions, such as hydroxide, wherein the ion exchange material comprises a polymer having the general formula P-COOH (in its less conductive state) the reactions are as follows:

$P-COOH + OH^- \rightarrow P-COO^- + H_2O$ (6)

At anode: $2H_2O - 4e^- + 44H^+ + O_2(g)$ (7)

$P-COO^- + H^+ \rightarrow P-COOH$ (8)

Thus the less conductive state of the ion exchange material is regenerated when the relevant chemical species is substantially absent. That is, upon removal of substantially most of the chemical species the less conductive state of the ion exchange material is reformed, as long as a liquid electrically bridges the two electrodes. By substantially absent is meant that the concentration of the chemical species is below the threshold level. This advantageously means that continuous monitoring of the chemical species is possible. If regeneration did not take place, and if no other steps were taken and if no other reactions were taking place, once all of the ion exchange material had been converted to its more conductive state the sensor cell would thereafter respond to any conductive solution, and would not selectively detect the chemical species with which we are concerned.

As mentioned above in connection with the acid and base sensors, the first electrode may be either the anode or the cathode; but to ensure regeneration of the ion exchange material the first electrode is preferably the cathode in the acid sensor, and the first electrode is preferably the anode in the base sensor. For applications where regeneration is not required, it may be preferred to reverse the polarities of the electrodes, viz so the first electrode is the anode in the acid sensor, and the cathode in the base sensor. With these arrangements reactions (3) and (6) are facilitated since hydrogen and hydroxide ions respectively are produced at the first electrode surface (by reactions (2) and (1)). Thus the ion exchange material on the first electrode in its less conductive state can react not only with hydrogen and hydroxide ions from the aqueous liquid, but also with those ions produced by electrolysis of water at the first electrode surface. Thus the ion exchange material becomes more conductive faster, and thus the sensor exhibits a shorter response time. In some embodiments according to the invention it is preferred to change the polarity of the electrodes part way through the detection. Preferably the polarity is changed so that first a rapid detection is achieved, and then regeneration. In other embodiments it is preferred to alternate the polarities of the electrodes on a regular cycle, for example by imposing a sinusoidal or square AC signal, or by powering the two electrodes with short voltage pulses, followed by a period during which the electrodes are left open circuited.

To detect an acid, the ion exchange material preferably comprises a functional group that has a dissociation factor, $pK_a$, which is numerically the same as, or greater than the pH of the solution to be detected. This achieves maximum conversion of the ion exchange material to its more conductive state. Similarly, the ion exchange material for a base sensor comprises a functional group that has a $pK_a$ numerically the same as, or less than, the pH of the liquid to be detected.

Preferably the electrochemical sensor cell comprises a second ion exchange material positioned in contact with the liquid, such that substantially all the electrical current passing through the electrochemical cell to the second electrode passes through the second ion exchange material. The electrical resistance of the second ion exchange material is preferably lower in the presence of the chemical species than in the absence of the chemical species. All preferred features for the first ion exchange material, with respect to the first electrode, are also preferred for the second ion exchange material with respect to the second electrode. The first and second ion exchange materials may be comprised of the same or different materials.

In one embodiment, the electrodes are preferably elongate and form part of an electrical circuit which can measure the position, along at least one of the electrodes, at which the chemical species is present. For example, the electrodes may have a length which is substantially greater, such as at least 100 times greater, often at least 1000 times greater, sometimes at least 10000 times greater than either of its other dimensions. Such an arrangement not only detects the presence of the chemical species but also its location.

The invention may be used to detect chemical species in a number of environments. For example, the electrodes may be placed adjacent a pipe or receptacle containing a liquid containing the chemical species. For example the electrodes may be wrapped around the pipe or container, or placed underneath the pipe or container, or where the pipe or container are buried in the soil, the electrodes may be buried adjacent the pipe or container. If any liquid leaks from the container or pipe and bridges the electrodes, it is detected.

The invention may be used to detect whether or at what concentration a chemical species is present in a liquid. This can be done simply by appropriately selecting the ion exchange material on the first electrode, and immersing the first and second electrodes in the liquid. The invention can also be used as a level sensor. This can be done by suspending the electrodes above a liquid containing the chemical species such that a rise in the level of the liquid is detected.

A preferred instance of detecting concentration is the determination of the state of charge of a battery or single cell, for example a lead-acid accumulator. Here the need for charging could be indicated by a sensor cell that indicated that pH had risen above a threshold value, or a more accurate state of charge could be indicated by monitoring pH over a range. A signal from the sensor cell could then simply activate a warning, or could be used to control a generator.

Referring now to the drawings FIG. 7 shows an article comprising a flat conductive polymer electrode 72. A copper mesh 74 and an insulating jacket 76 are applied to one side of electrode 72 and a layer of ion exchange material 78 is bonded to the opposite surface of the electrode 72. Where the article is to be used to detect the presence of hydrogen ions the ion exchange material may comprise units of the formula $P-C_5H_4N$. Where the article is to be used to detect the presence of basic liquids the ion exchange material may comprise units containing a carboxylic acid group or a phenol group. FIG. 8 shows an article which comprises a metallic support core 82 surrounded by a layer of conductive polymer 84 to which is bonded an ion exchange material 86 comprising units of the formula P—$C_5H_4N$.

FIG. 9 illustrates an apparatus which can be used in the invention to detect the presence of sufficient concentrations of hydrogen ions in a bath of liquid. The article of FIG. 8, shown in FIG. 9 as 90, is immersed in a bath of liquid 91. A counter, or second, electrode 92 is also immersed in the bath. A voltage 94 is applied to the electrodes so that electrode 90 is the cathode and the counter electrode 92 is the anode. An ammeter 96 is arranged to monitor the current. In the substantial absence of hydrogen ions the ion exchange material on the electrode 90 is less ionically conductive. Hence the current monitored on the ammeter 16 is small (of the order of $10^{-8}$ A/cm$^2$ in one embodiment) When the ion exchange material is exposed to hydrogen ions, e.g. when the liquid comprises an acid, the material becomes more ionically conductive, and a current of the order of $10^{-4}$ A/cm$^2$ may be monitored on the ammeter 96.

FIG. 10 is a cross-sectional view of a device which incorporates the article of FIG. 8 and which can be used to detect the presence of hydrogen ions. The device comprises two electrode wires 100 according to the FIG. 8 and two return wires 101 comprising a metallic core 102 having an insulating jacket 104. A braid or other jacket (not shown) may surround the wires. A braid may provide mechanical protection and may also hold the wires together.

FIG. 11 is a schematic drawing showing a circuit in which articles according to the invention may be incorporated. The circuit comprises a source wire 11, locating wire 112, a return wire 114, a constant current power supply, and a voltmeter. Wires 110 and 112 are initially separated from each other but can be connected by an event Ek such as a leak of electrolyte. When connection is made, a test circuit is formed comprising wires 110, 112 and the event E. A constant current I is driven through that circuit. Locating wire 112 has a known impedance which is constant or varies in a known way along its length, and together with return wire 114 forms a reference circuit, in which the voltage measuring device is included. Provided the impedance values of all the elements in the reference circuit are known, and given the voltage measurement of the reference circuit and the known current flowing through the locating wire 112 it is possible to determine the position of event E. In the circuit illustrated, all of the current I will flow through event E, and if a high impedance voltmeter is used a current substantially equal to I may be assumed to flow along locating member 112 between a first point 116 and a second point 118. The voltage drop measured by the voltmeter will proportional (or some other known function) of the distance between the first and second points. The positions of the power source and voltmeter may be reversed, but then estimation of the currents in the various paths may be more difficult.

A device as shown in FIG. 10, for example, may be included in the circuit of FIG. 11, articles 100 providing the source and locating wires 110 and 112, and one of the insulated wires 101 providing the return wire 114. The event E which causes connection of the two wires 100 is the increase in the polymeric member's ionic conductivity, resulting from the presence of the chemical species. For an acid sensor this increased conductivity is caused by the presence of the hydrogen ions.

An embodiment of the invention is now described with reference to the following example:

EXAMPLE 8

Ion exchange material may also be applied to a wire. As an example, a solution was prepared from 51.3 mole percent 4-vinylpyridine, 31.0% 2-ethylhexyl acrylate, 3.7% technical divinylbenzene, 4.0% benzoyl peroxide, and 10% of a linear polymer for thickening. This polymer consisted of 65 mole percent 4-vinylpyridine and 35% 2-ethylhexyl acrylate, was produced in a free radical polymerization in a preceding step, and had, a weight average molecular weight of approximately 200,000. Ten percent of this thickening polymer produced a solution of 800 cps. A 1.10 mm diameter conductive polymer wire (with a 24 gauge metallic core) was dipped in this thickened solution and drawn upward into and through a ten foot (3.3 m) heating tower held at 135° C. The wire with a $1.2 \times 10^{-4}$ m coating of ion exchange material was spooled at room temperature and samples could be placed in 1 M HCl to produce the pyridinium chloride form of the ion exchange layer.

EXAMPLE 9

Source and locating wires as in FIG. 8 for an acid sensor were prepared using a Copel wire (3 ohm per ft., 0.1 ohm per cm) covered with a conductive polymer jacket comprising a linear low density polyethylene carbon black blend. The ion exchange material bonded to this wire was 100 microns thick and comprised a terpolymer of 35 mole percent 4-vinylpyridine, 67 mole percent ethylhexyl acrylate, and 3 mole percent technical divinylbenzene. These wires were incorporated in a sensor as described in FIG. 10. After submersion of a 4 inch (10 cm) length of sensor (or 3 cm$^2$ area on each electrode) in tap water (pH=6), for several days the current was found to be $2 \times 10^{-8}$ A. This sample was then exposed to a 3M HCL liquid, and the current measured as a function of time. The current reached $3 \times 10^{-4}$ A within 2 minutes, and was rinsed and replaced in tap water to regenerate. After 20 minutes the current was reduced to $1.5 \times 10^{-5}$ A, and continued to drop over the next hours and days to $4 \times 10^{-7}$ A. A representative response/regeneration curve is shown in FIG. 12.

EXAMPLE 10

A second specific example is illustrated in FIGS. 13 and 14. Here, some operation connected with a battery 130 is controlled. The battery may be of any type, and the one illustrated is a lead-acid accumulator comprising six cells 131, three only of which are shown. The battery has two terminals 132 connected to electrode plates 133, of which there may be many, but two are shown. A sensor cell 134 is shown immersed in the electrolyte 135 of the battery. The sensor cell, which may be of the type described above, preferably comprises a casing 136, permeable to the electrolyte 135, containing first and second electrodes 137,138, at least one of which is surrounded by an ion exchange resin 139. If desired one of the battery electrodes 133 may function also as one of the sensor cell electrodes.

A known voltage is applied to the first and second electrodes 137,138 and the resistance or impedance between them is measured. The resistance will depend on the resistance of the ion-exchange resin 139, as explained above. Thus, an indication of the pH (or other concentration) will be provided. The sensor cell 134 may be positioned such that the pH measured gives an accurate indication of the overall state of charge of the battery.

A sensor cell 134 may be used to regulate charging, discharging or heating of a battery. FIG. 14 shows its use in regulating charging, in a circuit that may be useful in automobiles such as cars or trucks or other means of transport.

Battery 140 has terminals 141, one of which is connected to earth 142, and the other to various electrical devices, represented generally as load 143. A generator 144 is connected between earth 142 and the live side of the battery. A computer, or other control system, 145 controls the generator 144 in response to a signal from the sensor cell 134. A power supply 146 supplies a fixed voltage to the sensor cell electrodes 137,138. The fixed voltage, which is preferable from 2–9 volts, especially from 3–7 volts (in the case of a normally 12 volt lead-acid accumulator) may be tapped from the battery 140 itself since that voltage will be available in all but the lowest state of discharge. The computer 145 measures current in the sensor cell circuit, for example by measuring the voltage drop across a resistor 66. The resistance of the sensor cell 134 will depend on the pH (or other concentration) within the battery 140, and is represented by a variable resistance 147. The value of variable resistance 147 will affect the voltage drop across resistor 148. The signal that the computer 145 receives from the sensor cell is used to control the output of generator 144. In this way, charging of the battery can be limited or stopped when its pH reaches a sufficiently low value. This may be desirable for extending the cycle life of batteries.

It can be seen that the power supply 146 is isolated from the anode and cathode of the battery 140. In spite of this isolation, some undesirable current loops can form which may affect the current flowing through the sensor cell. In general, the situation can be improved by employing a sensor cell powered by a periodic waveform, for example alternating voltage and having some means of DC isolation, for example a capacitor. Since any undesirable voltages due to the battery that may be impressed on the sensor cell circuit will be DC they will have no effect on current flowing in the sensor cell. An alternating voltage may be generated simply by standard techniques, and components may be present to protect the circuit against surge or transients etc., for example on starting of a car engine.

In this example and in other embodiments the effect of the battery may be reduced, at least to some extent by making the measurements of the sensor cell when the battery 146 is open circuit. The battery could be switched, for example automatically, to open circuit periodically for a short period to allow the sensor cell to be monitored.

In general it may be desirable that the sensor cell be shielded from any current resulting from operation of the battery 146 itself. One possibility is to provide one of the electrodes 137,138 as a hollow cylinder, and the other positioned within it. The annular space between the two could contain the ion exchange resin.

Where the sensor cell is used with a battery (as illustrated) rather than with a single cell it may in general be positioned in any of the cells, and the electrodes 137,138 of the sensor cell may have any suitable spatial relationship with respect to the anodes and cathodes of the battery. Where the power supply 146 for the sensor cell is independent of the battery, in general no series problems will arise. However, if the power supply of the sensor cell is connected to the battery (for example by their having a common earth) more care may be required to prevent unwanted current loops resulting in inaccurate signals from the sensor cell. Also, different results may be obtained depending on which of the cells of the battery contains the sensor cell. This is because the potential of the anodes and cathodes of each cell will be different with respect to the common earth to which the sensor cell is connected.

This is illustrated in FIG. 15a which shows a sensor cell having a common earth with that of the battery and which show the sensor cell positioned in the cell of the battery closest to the common earth, as indicated by the n cells to one side of it. That position is preferred since undesired current loops are minimized. In FIG. 15a the sensor is designed for alternating voltage and a capacitor is provided to prevent direct current. FIG. 15a could be altered such that the sensing electrode is powered by a direct voltage where the sensor can be a cathode or anode. Some undesired current loops may exist in these circuits, but they may however be satisfactory for some purposes. The use of an alternating voltage in the sensor cell, as mentioned above, may be used to advantage.

FIG. 15b shows a sensor cell having one electrode in common with an electrode of one of the cells of the battery under test. The sensor cell may be positioned in any cell of the battery, as is indicated by the variable number of battery cells either side of it. Again, an alternating voltage could be used for the sensor cell.

We claim:

1. A method of replacing an ionic species in an ion exchange material containing the ionic species, which method comprises passing a current through a first electrochemical cell which comprises:
   (1) a first electrode;
   (2) an ion exchange material A which
      (a) contains an ionic species $I_{1A}$, and
      (b) is secured to an in electrical contact with the first electrode at an interface;
   (3) a second electrode; and
   (4) an electrolyte which electrically connects the first and second electrodes and contains an ionic species $I_{3A}$, which species $I_{3A}$ has the same polarity as the species $I_{1A}$ and maintains its polarity at the interface between the first electrode and the ion exchange material A;

and in which cell an electrochemical reaction takes place at the interface between the first electrode and the ion exchange material A and generates an ionic species $I_{2A}$ which has a polarity opposite to the polarity of the species $I_{1A}$ and causes the ionic species $I_{1A}$ to be replaced by ionic species $I_{3A}$.

2. A method according to claim 1, which additionally comprises the subsequent step of placing the first electrode and the ion exchange material A, which is secured to the first electrode and contains the species $I_{3A}$, in a liquid which contains an ionic species $I_{4A}$ having the same polarity as the species $I_{3A}$, thereby replacing the species $I_{3A}$ by the species $I_{4A}$.

3. A method according to claim 2, which additionally comprises the step of passing current through a second electrochemical cell which comprises:
   (1) the first electrode, the polarity of the first electrode in the second electrochemical cell being opposite from the polarity of the first electrode in the first electrochemical cell;

(2) the ion exchange material A which contains the species $I_{4A}$ and which is secured to and in electrical contact with the first electrode at the interface;

(3) a further electrode; and (4) an electrolyte which electrically connects the first and further electrodes, and which, at the interface between the first electrode and the ion exchange material, undergoes an electrochemical reaction which generates an ionic species $I_{5A}$ which causes species $I_{4A}$ to be replaced by another ionic species.

4. A method according to claim 1, which additionally comprises the step of passing current through a third electrochemical cell which comprises:

(1) the first electrode, the polarity of the first electrode in the third electrochemical cell being opposite from the polarity of the first electrode in the first electrochemical cell;

(2) the ion exchange material which contains the species $I_{3A}$ which is secured to and in electrical contact with the first electrode at the interface;

(3) a further electrode; and (4) an electrolyte which electrically connects the first and further electrodes, and which, at the interface between the first electrode and the ion exchange material A, undergoes an electrochemical reaction which generates an ionic species $I_{6A}$ which replaces the ionic species $I_{3A}$.

5. A method according to claim 1, wherein (i) the electrochemical cell additionally comprises a second ion exchange material B which (a) contains an ionic species $I_{1B}$ and (b) is secured to and in contact with the second electrode at an interface; and (ii) an electrochemical reaction takes place at the interface between the second electrode and the ion exchange material B and generates an ionic species $I_{2B}$ which causes the species $I_{1B}$ to be replaced by another ionic species.

6. A method according to claim 1, wherein the first electrode comprises a conductive polymer, the ion exchange material being secured to the conductive polymer.

7. A method according to claim 1 wherein substantially all of the ionic species $I_{2A}$ passes through the ion exchange material.

8. A method according to claim 1 wherein the electrolyte comprises an aqueous solution and ionic species $I_{2A}$ is a product of the electrolysis of water.

* * * * *